United States Patent
Chan et al.

(10) Patent No.: US 7,345,770 B2
(45) Date of Patent: Mar. 18, 2008

(54) OPTICAL IMAGE MEASURING APPARATUS AND OPTICAL IMAGE MEASURING METHOD FOR FORMING A VELOCITY DISTRIBUTION IMAGE EXPRESSING A MOVING VELOCITY DISTRIBUTION OF THE MOVING MATTER

(75) Inventors: Kinpui Chan, Yamagata (JP);
Masahiro Akiba, Yamagata (JP);
Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 151 days.

(21) Appl. No.: 11/265,309

(22) Filed: Nov. 3, 2005

(65) Prior Publication Data
US 2006/0100528 A1    May 11, 2006

(30) Foreign Application Priority Data
Nov. 8, 2004 (JP) ............................. 2004-323342
Apr. 5, 2005 (JP) ............................. 2005-109247

(51) Int. Cl.
*G01B 11/24* (2006.01)
(52) U.S. Cl. ....................................... 356/489; 356/497
(58) Field of Classification Search ................ 356/479, 356/489, 497
See application file for complete search history.

(56) References Cited

U.S. PATENT DOCUMENTS

| | | | |
|---|---|---|---|
| 5,501,226 A * | 3/1996 | Petersen et al. | ............ 600/504 |
| 5,991,697 A * | 11/1999 | Nelson et al. | ................ 702/49 |
| 6,465,147 B1 * | 10/2002 | Lee et al. | ............... 430/270.1 |
| 6,944,551 B2 * | 9/2005 | Chen et al. | ................... 702/49 |
| 7,095,503 B2 * | 8/2006 | Kim et al. | .................. 356/497 |

FOREIGN PATENT DOCUMENTS

JP 2001-330558 11/2001

(Continued)

OTHER PUBLICATIONS

N. Tanno; "Optical coherence tomography and its application to living-body imaging;" *Kogaku (Japanese Journal of Optics)*; vol. 28; No. 3; 1999; pp. 116-125, Cover page and partial translation (9 Sheets total.)/Discussed in the specification.

(Continued)

*Primary Examiner*—Samuel A. Turner
(74) *Attorney, Agent, or Firm*—Edwards Angell Palmer & Dodge LLP

(57) ABSTRACT

An optical image measuring apparatus capable of speedily measuring a velocity distribution image of a moving matter. Including a broad-band light source, lenses for increasing a beam diameter, a polarizing plate converting the light beam to linearly polarized light, and a half mirror, a wavelength plate converting the reference light to circularly polarized light, the half mirror superimposing the signal light whose frequency is partially shifted by the moving matter in the object and the reference light is circularly polarized light to produce superimposed light including interference light, CCDs for receiving different polarized light components of the interference light, and outputting detection signals including interference frequency components corresponding to beat frequencies of the interference light, and a signal processing portion for forming velocity distribution image based on interference frequency component corresponding to a beat frequency equal to an intensity modulation frequency of the light beam.

50 Claims, 13 Drawing Sheets

FOREIGN PATENT DOCUMENTS

| | | |
|---|---|---|
| JP | 2001-526650 | 12/2001 |
| JP | 2002-504894 | 2/2002 |
| JP | 2002-214130 | 7/2002 |

OTHER PUBLICATIONS

T. Nakajima; "Principle and application of the optical heterodyne method;" *Optical Heterodyne Technology (revised edition) New technology communications*; 2003; pp. 1-10, Cover page and partial translation (9 Sheets total).

K.P. Chan, et al; "Micrometre-resolution, optical imaging of objects through highly scattered media using a heterodyne detector array;" *Electronics Letters*; vol. 30; No. 21; Oct. 13, 1994; pp. 1753-1754./ Discussed in the specification.

A. Major, et al.; "Microvascular Photodynamic Effects Determined In Vivo Using Optical Doppler Tomography;" *IEEE Journal of Selected Topics in Quantum Electronics*; vol. 5; No. 4; Jul./Aug. 1999; pp. 1168-1175 (4 Sheets total.)/Discussed in the specification.

M. Akiba, et al.; "Real-Time, Micrometer Depth-Resolved Imaging by Low-Coherence Reflectometry and a Two-Dimensional Heterodyne Detection Technique;" *Jpn. J. Appl. Phys.*; vol. 39; 2000; pp. L1194-L1196 (3 Sheets total.)/Discussed in the specification.

* cited by examiner

OPTICAL IMAGE MEASURING APPARATUS AND OPTICAL IMAGE MEASURING METHOD FOR FORMING A VELOCITY DISTRIBUTION IMAGE EXPRESSING A MOVING VELOCITY DISTRIBUTION OF THE MOVING MATTER

BACKGROUND OF THE INVENTION

1. Field of the Invention

The present invention relates to an optical image measuring apparatus employing a structure in which an object to be measured which is particularly a light scattering medium is irradiated with a light beam and a surface form or inner form of the object to be measured is measured based on a reflected light beam or a transmitted light beam to produce an image of a measured form, and to an optical image measuring method for the optical image measuring apparatus. In particular, the present invention relates to a technique for producing an image expressing a moving velocity of a moving matter such as a fluid flowing through the object to be measured, which is used for an optical image measuring apparatus for producing an image of the object to be measured by using an optical heterodyne detection method and an optical image measuring method for the optical image measuring apparatus.

2. Description of the Related Art

In recent years, attention has been given to optical imaging technique that produces an image of a surface or inner portion of an object to be measured using a laser light source or the like. This optical imaging technique is not hazardous to human bodies in contrast to the conventional X-ray CT. Therefore, the development of applications in the medical field has been particularly expected.

An example of a typical method of the optical imaging technique is a low coherent interference method (also called 'optical coherence tomography' or the like). This method uses the low coherence of a broad-band light source having a broad spectral width, such as a super luminescent diode (SLD). According to this method, reflection light from an object to be measured or light transmitted therethrough can be detected at superior distance resolution on the order of μm (for example, see Naohiro Tanno, "Kogaku" (Japanese Journal of Optics), Volume 28, No. 3, 116 (1999)).

FIG. 14 shows a basic structure of a conventional optical image measuring apparatus based on a Michelson interferometer, as an example of an apparatus using the low coherent interference method. An optical image measuring apparatus 200 includes a broad-band light source 201, a mirror 202, a beam splitter 203, and a photo detector 204. An object to be measured 205 is made of a scattering medium. A light beam from the broad-band light source 201 is divided by the beam splitter 203 into two, that is, reference light R propagating to the mirror 202 and signal light S propagating to the object to be measured 205. The reference light R is light reflected by the beam splitter 203. The signal light S is light transmitted through the beam splitter 203.

Here, as shown in FIG. 14, a propagating direction of the signal light S is set as a z-axis direction and a plane orthogonal to the propagating direction of the signal light S is defined as an x-y plane. The mirror 202 is movable in a direction indicated by a double-headed arrow in FIG. 14 (z-scanning direction).

The reference light R is subjected to a Doppler frequency shift through when reflected by the z-scanning mirror 202. On the other hand, the signal light S is reflected from the surface of the object to be measured 205 and from the inner layers thereof when the object to be measured 205 is irradiated with the signal light S. The object to be measured 205 is made of the scattering medium, so reflection light of the signal light S may be a diffusing wave having random phases. The signal light propagating through the object to be measured 205 and the reference light that is reflected by the mirror 202 to be subjected to the frequency shift are superimposed on each other by the beam splitter 203 to produce interference light.

In the image measurement using such a low coherent interference method, interference occurs only when a difference in optical path length between the signal light S and the reference light R is within the coherence length (coherent distance) on the order of μm of the light source. In addition, only the component of the signal light S whose phase is correlated to that of the reference light R interferes with the reference light R. That is, only the coherent signal light component of the signal light S selectively interferes with the reference light R. Based on their principles, the position of the mirror 202 is moved by the z-scanning to vary the optical path length of the reference light R, so that a reflectance profile of the inner layers of the object to be measured 205 is measured. The object to be measured 205 is also scanned with the irradiated signal light S in an x-y plane direction. The interference light is detected by the photo detector 204 during such scanning in the z-direction and the x-y plane direction. An electrical signal (heterodyne signal) outputted as a detection result is analyzed to obtain a two-dimensional sectional image of the object to be measured 205 (see Naohiro Tanno, "Kogaku" (Japanese Journal of Optics), Volume 28, No. 3, 116 (1999)).

Assume that an intensity of the reference light R and an intensity of the signal light S which are superimposed by the beam splitter 203 are given by $I_r$ and $I_s$, respectively, and a frequency difference between the reference light R and the signal light S and a phase difference therebetween are given by $f_{if}$ and $\Delta\theta$, respectively. In this case, a heterodyne signal as expressed by the following expression is outputted from the photo detector (for example, see Yoshizawa and Seta "Optical Heterodyne Technology (revised edition)", New Technology Communications (2003), p. 2).

Expression (1)

$$i(t) \propto I_r + I_s + 2\sqrt{I_r I_s} \cos(2\pi f_{if} t + \Delta\theta) \qquad (1)$$

The third term of the right side of the expression (1) indicates an alternating current electrical signal and the frequency $f_{if}$ thereof is equal to the frequency of beat caused from the interference between the reference light R and the signal light S. The frequency $f_{if}$ of an alternating current component of the heterodyne signal is called a beat frequency or the like. The first and second terms of the right side of the expression (1) indicate the direct current components of the heterodyne signal and correspond to a signal intensity of background light of interference light.

However, when the two-dimensional cross sectional image is obtained by the conventional low coherent interference method, it is necessary to scan the object to be measured 205 with a light beam and to successively detect reflection light waves from respective regions of the object to be measured 205 in a depth direction (z-direction) and a sectional direction (x-y plane direction). Therefore, the measurement of the object to be measured 205 requires a long time. In addition, it is hard to shorten a measurement time in view of measurement fundamentals.

In views of such problems, an optical image measuring apparatus for shortening a measurement time has been proposed. FIG. 15 shows a fundamental structure of an example of such an apparatus. As shown in FIG. 15, an optical image measuring apparatus 300 includes a broadband light source 301, a mirror 302, a beam splitter 303, a two-dimensional photo sensor array 304 serving as a photo detector, and lenses 306 and 307. A light beam emitted from the light source 301 is converted into a parallel light flux by the lenses 306 and 307 and a beam diameter thereof is widened thereby. Then, the parallel light flux is divided into two, that is, the reference light R and the signal light S by the beam splitter 303. The reference light R is subjected to Doppler frequency shift through z-scanning with the mirror 302. On the other hand, the signal light S is incident on the object to be measured 305 over a broad area of the x-y plane because the beam diameter is widened. Therefore, the signal light S becomes reflection light including information related to the surface and inner portion of the object to be measured 305 over a wide area. The reference light R and the signal light S are superimposed on each other by the beam splitter 303 and detected by elements (photo sensors) arranged in parallel on the two-dimensional photo sensor array 304. Thus, it is possible to obtain a two-dimensional cross sectional image of the object to be measured 305 in real time without light beam scanning.

An apparatus described in K. P. Chan, M. Yamada, and H. Inaba, "Electronics Letters", Vol. 30, 1753 (1994) has been known as such a non-scanning type optical image measuring apparatus. In the apparatus described in the same document, a plurality of heterodyne signals outputted from a two-dimensional photo sensor array are inputted to signal processing systems arranged in parallel to detect the amplitude and phase of each of the heterodyne signals.

However, when the spatial resolution of an image is increased, it is necessary to increase a number of elements of the array. In addition, it is necessary to prepare a signal processing system including a number of channels corresponding to the number of elements. Therefore, it is supposedly hard to actually use the apparatus in fields that require a high resolution image, such as a medical field and an industrial field.

Thus, the inventors of the present invention have proposed the following non-scanning type optical image measuring apparatus in JP 2001-330558 A (claims and specification paragraphs [0068] to [0084], and FIG. 1). The optical image measuring apparatus according to this proposal includes a light source for emitting a light beam, an interference optical system, and a signal processing portion. In the interference optical system, the light beam emitted from the light source is divided into two, that is, signal light propagating through an examined object arrangement position in which an object to be examined is arranged and reference light propagating on an optical path different from an optical path passing through the examined object arrangement position. The signal light propagating through the examined object arrangement position and the reference light propagating on the different optical path are superimposed on each other to produce interference light. The interference optical system includes a frequency shifter, light cutoff devices, and photo sensors. The frequency shifter shifts a frequency of the signal light and a frequency of the reference light relative to each other. In order to receive the interference light in the interference optical system, the interference light is divided into two parts. The light cutoff devices periodically cut off the two divided parts of the interference light to generate two interference light pulse trains with a phase difference of 90 degrees therebetween. The photo sensors respectively receive the two interference light pulse trains. The photo sensors each have a plurality of light receiving elements which are spatially arranged and separately detect light receiving signals. The signal processing portion combines the plurality of light receiving signals detected by the photo sensors to generate signals of the signal light which correspond to respective points of interest of a surface or inner layers of the object to be examined which is arranged in the examined object arrangement position on a propagating path of the signal light.

In the optical image measuring apparatus, an optical path of the interference light composed of the reference light and the signal light is divided into two optical paths, and the light cutoff device and the photo sensor (two-dimensional photo sensor array) are disposed on each of the two optical paths. A phase difference of $\pi/2$ is set between sampling periods of the light cutoff devices disposed on the two optical paths. Therefore, intensities of the signal light and reference light which compose background light of the interference light, and phase quadrature components (sine component and cosine component) of the interference light, are detected. Further, an intensity of the background light included in outputs from the photo sensors is subtracted from the outputs of the photo sensors to calculate two phase quadrature components of the interference light. An amplitude of the interference light is acquired based on a result obtained by calculation.

An available image sensor such as a charge-coupled device (CCD) camera has been widely used for the two-dimensional photo sensor array of the optical image measuring apparatus as described above. However, up to now, a problem has been recognized that a currently available CCD camera cannot follow the beat frequency of a heterodyne signal which is the order of several kHz to several MHz because of the low frequency response characteristic thereof. The feature of the optical image measuring apparatus which is proposed by the inventors of the present invention and described in JP 2001-330558 A (claims, specification paragraphs [0068] to [0084], and FIG. 1) is to perform the measurement using the low frequency response characteristic based on the sufficient recognition of the problem.

With respect to the above-mentioned optical image measuring technique, a technique for measuring the velocity of a moving matter in the object to be measured, such as the flow velocity of blood flowing through a blood vessel of a living tissue, has been developed. For example, a method described in "IEEE Journal of Selected Topics in Quantum Electronics, Vol. 5, No. 4, July/August 1999" is to measure a velocity component in a certain direction, of the moving matter in the object to be measured, that is, a directional component of a three-dimensional velocity vector of the moving matter.

According to a technique for measuring all three components of a three-dimensional velocity vector of a moving matter as disclosed in JP 2002-214130 A (claims, specification paragraphs [0021] and [0027], and FIG. 3), a light wave from a coherent light source is divided into four light waves. Three light waves pass through three frequency shifters, respectively, to become a first light wave, a second light wave, and a third light wave. A remaining light wave is incident as reference light on a photo detector without passing through a frequency shifter to become a fourth light wave. The first light wave is incident on an objective lens along an optical axis of the objective lens. The second light wave is incident on a peripheral portion of the objective lens and a light wave exiting therefrom intersects the first light wave at an angle $\theta$ formed on an XZ-plane. The third light wave is incident on a peripheral portion of the objective lens and a light wave exiting therefrom intersects the first light wave at an angle θ formed on a YZ-plane. When a scattering medium which is a living tissue is moving at a predetermined velocity, scattering light caused by the scattering medium is detected as a heterodyne signal by the photo detector and subjected to frequency analysis by an RF spectrum analyzer.

However, according to the technique described in JP 2002-214130 A, when the object to be measured is to be measured over a wide range, a mechanism for moving the object to be measured to scan measurement positions (sample stage) is necessary, which leads to a problem in that the measurement takes a long time.

When the technique described in JP 2002-214130 A is to be applied to living tissue measurement, in particular, when the flow velocity of blood flowing through the retina blood vessel of a human eye is to be measured, it may be difficult to scan the measurement positions by moving the living tissue itself in view of an apparatus structure, measurement accuracy, and the like.

SUMMARY OF THE INVENTION

The present invention has been made in view of the above-mentioned circumstances. An object of the present invention is to provide an optical image measuring apparatus capable of speedily measuring an object to be measured over a wide range in order to measure an image expressing a velocity distribution of a moving matter in the object to be measured, and an optical image measuring method for the optical image measuring apparatus.

Another object of the present invention is to provide an optical image measuring apparatus capable of effectively measuring an object to be measured over a wide range in order to measure an image expressing a distribution such as a flow velocity distribution of blood flowing through a blood vessel of a living tissue, and an optical image measuring method for the optical image measuring apparatus.

In order to achieve the above object, according to a first aspect of the present invention, there is provided an optical image measuring apparatus, characterized by including: light beam outputting means for outputting a light beam whose intensity is periodically modulated at a modulation frequency, the light beam being low-coherent; increasing means for increasing a beam diameter of the outputted light beam; a first converting means for converting a polarization characteristic of the light beam to linear polarization; light beam dividing means for dividing the light beam into signal light propagating to an object to be measured and reference light propagating to a reference object; a second converting means for converting a polarization characteristic of one of the signal light and the reference light, which are linearly polarized light; superimposing means for superimposing the signal light whose part propagating through a moving matter in the object to be measured is subjected to frequency shift and the reference light propagating through the reference object on each other to produce superimposed light including interference light having a beat frequency corresponding to a quantity of the frequency shift, in which one of the signal light and the reference light is the linearly polarized light acquired by the first converting means and the other thereof has the polarization characteristic acquired by the second converting means; at least one two-dimensional photo-detection means for receiving a plurality of different polarized light components of the interference light included in the produced superimposed light, and outputting a detection signal including interference frequency components corresponding to beat frequencies of the interference light; and image forming means for forming a velocity distribution image expressing a moving velocity distribution of the moving matter based on an interference frequency component corresponding to a beat frequency substantially equal to the modulation frequency at which the intensity of the light beam is modulated by the light beam outputting means, among the interference frequency components included in the outputted detection signal.

Further, according to a second aspect of the present invention, there is provided an optical image measuring apparatus according to the first aspect, characterized by further including: a first modulation frequency changing means for changing the modulation frequency at which the intensity of the light beam is modulated by the light beam outputting means, and characterized in that: the two-dimensional photo-detection means receives a plurality of superimposed light beams produced from the light beam whose intensity is modulated at different modulation frequencies changed by the first modulation frequency changing means and outputs a plurality of detection signals, each of which includes the interference frequency components; the image forming means forms a plurality of two-dimensional images, each of which is based on an interference frequency component corresponding to a beat frequency substantially equal to a modulation frequency at which the intensity of the light beam is modulated by the light beam outputting means, in accordance with each of the plurality of outputted detection signals; and the image forming means synthesizes the plurality of formed two-dimensional images with one another to form a two-dimensional velocity distribution image.

Further, according to a third aspect of the present invention, there is provided an optical image measuring apparatus according to the first or second aspect, characterized by further including a polarization beam splitter for separating an S-polarized light component and a P-polarized light component of the interference light included in the superimposed light produced by the superimposing means from each other, and characterized in that the two-dimensional photo-detection means is provided on each of optical paths of the S-polarized light component and the P-polarized light component which are separated from each other.

Further, according to a fourth aspect of the present invention, there is provided an optical image measuring apparatus, characterized by including: a light source for outputting a light beam which is low-coherent; increasing means for increasing a beam diameter of the outputted light beam; light beam dividing means for dividing the light beam whose beam diameter is increased into signal light propagating to an object to be measured and reference light propagating to a reference object; superimposing means for superimposing the signal light whose part propagating through a moving matter in the object to be measured is subjected to frequency shift and the reference light propagating through the reference object on each other to produce superimposed light including interference light having a beat frequency corresponding to a quantity of the frequency shift; intensity modulating means for periodically modulating an intensity of the produced superimposed light; two-dimensional photo-detection means for receiving the superimposed light whose intensity is modulated, and outputting a detection signal including interference frequency components corresponding to beat frequencies of the interference light; and image forming means for forming a velocity distribution image expressing a moving velocity distribution of the moving matter based on an interference frequency component corresponding to a beat frequency substantially equal to a modulation frequency at which the intensity of the superimposed light is modulated by the intensity modulating means, among the interference frequency components included in the outputted detection signal.

Further, according to a fifth aspect of the present invention, there is provided an optical image measuring apparatus according to the fourth aspect, characterized by further including a second modulation frequency changing means for changing the modulation frequency at which the intensity of the superimposed light is modulated by the intensity modulating means, and characterized in that: the two-dimensional photo-detection means receives a plurality of superimposed light beams whose intensity is modulated at different modulation frequencies changed by the second modulation frequency changing means and outputs a plurality of detection signals, each of which includes the interference frequency components; the image forming means forms a plurality of two-dimensional images, each of which is based on an interference frequency component corresponding to a beat frequency substantially equal to a modulation frequency at which an intensity of a superimposed light beam is modulated by the intensity modulating means in accordance with each of the plurality of outputted detection signals; and the image forming means synthesizes the plurality of formed two-dimensional images with one another to form a two-dimensional velocity distribution image.

Further, according to a sixth aspect of the present invention, there is provided an optical image measuring apparatus according to the fourth or fifth aspect, characterized by further including superimposed light dividing means for dividing an optical path of the superimposed light produced by the superimposing means into a plurality of optical paths, and characterized in that the two-dimensional photo-detection means receives each of a plurality of superimposed light beams propagating on the plurality of optical paths and outputs a detection signal.

Further, according to a seventh aspect of the present invention, there is provided an optical image measuring apparatus according to any one of the first to sixth aspects, characterized by further including optical path length changing means for changing an optical path length of the reference light to change a measurement depth of the object to be measured, and characterized in that: the two-dimensional photo-detection means outputs a plurality of detection signals corresponding to a plurality of measurement depths which are different from one another based on optical path lengths changed by the optical path length changing means; the image forming means forms a plurality of two-dimensional velocity distribution images corresponding to the measurement depths based on the outputted detection signals corresponding to the plurality of measurement depths; and the image forming means arranges the plurality of formed two-dimensional velocity distribution images in a measurement depth direction and performs image processing on the arranged two-dimensional velocity distribution images to form a three-dimensional velocity distribution image.

Further, according to an eighth aspect of the present invention, there is provided an optical image measuring apparatus according to any one of the first to seventh aspects, characterized by further including frequency shifting means for shifting a frequency of the signal light and a frequency of the reference light relative to each other.

Further, according to a ninth aspect of the present invention, there is provided an optical image measuring apparatus according to any one of the first to eighth aspects, characterized by further including display means for displaying the velocity distribution images formed by the image forming means.

Further, according to a tenth aspect of the present invention, there is provided an optical image measuring apparatus according to any one of the first to ninth aspects, characterized in that: wherein the object to be measured comprises at least one of a retina of an eye to be examined and a lower tissue of the retina; and the moving matter comprises one of blood flowing through a blood vessel of at least one of the retina and the lower tissue of the retina and blood containing a contrast agent injected in advance.

Further, according to an eleventh aspect of the present invention, there is provided an optical image measuring method, characterized by including: a light beam outputting step for outputting a light beam whose intensity is periodically modulated at a modulation frequency, the light beam being low-coherent; an increasing step for increasing a beam diameter of the outputted light beam; a first converting step for converting a polarization characteristic of the light beam to linear polarization; a light beam dividing step for dividing the light beam into signal light propagating to an object to be measured and reference light propagating to a reference object; a second converting means for converting a polarization characteristic of one of the signal light and the reference light, which are linearly polarized light; a superimposing step for superimposing the signal light whose part propagating through a moving matter in the object to be measured is subjected to frequency shift and the reference light propagating through the reference object on each other to produce superimposed light including interference light having a beat frequency corresponding to a quantity of the frequency shift, in which one of the signal light and the reference light is the linearly polarized light acquired in the first converting step and the other thereof has the polarization characteristic acquired in the second converting step; a detection step for receiving a plurality of different polarized light components of the interference light included in the produced superimposed light by at least one two-dimensional photo-detection means, and outputting a detection signal including interference frequency components corresponding to beat frequencies of the interference light; and an image forming step for forming a velocity distribution image expressing a moving velocity distribution of the moving matter based on an interference frequency component corresponding to a beat frequency substantially equal to the modulation frequency at which the intensity of the light beam is modulated in the light beam outputting step, among the interference frequency components included in the outputted detection signal.

Further, according to a twelfth aspect of the present invention, there is provided an optical image measuring method according to the eleventh aspect, characterized in that: the light beam outputting step includes outputting the light beam while changing the modulation frequency at which the intensity of the light beam is modulated; the detection step includes receiving a plurality of superimposed light beams produced from the light beam whose intensity is modulated at different modulation frequencies changed in the light beam outputting step and outputting a plurality of detection signals, each of which includes the interference frequency components; and the image forming step includes: forming a plurality of two-dimensional images, each of which is based on an interference frequency component corresponding to a beat frequency substantially equal to a modulation frequency at which the intensity of the light beam is modulated in the light beam outputting step, in accordance with each of the plurality of outputted detection signals; and synthesizing the plurality of formed two-dimensional images with one another to form a two-dimensional velocity distribution image.

Further, according to a thirteenth aspect of the present invention, there is provided an optical image measuring method, characterized by including: a step of outputting a light beam which is low-coherent; an increasing step for increasing a beam diameter of the outputted light beam; a light beam dividing step for dividing the light beam whose beam diameter is increased into signal light propagating to an object to be measured and reference light propagating to a reference object; a superimposing step for superimposing the signal light whose part propagating through a moving matter in the object to be measured is subjected to frequency shift and the reference light propagating through the reference object on each other to produce superimposed light including interference light having a beat frequency corresponding to a quantity of the frequency shift; an intensity modulating step for periodically modulating an intensity of the produced superimposed light; a detection step for receiving the superimposed light whose intensity is modulated by a two-dimensional photo-detection means, and outputting a detection signal including interference frequency components corresponding to beat frequencies of the interference light; and an image forming step for forming a velocity distribution image expressing a moving velocity distribution of the moving matter based on an interference frequency component corresponding to a beat frequency substantially equal to a modulation frequency at which the intensity of the superimposed light is modulated in the intensity modulating step, among the interference frequency components included in the outputted detection signal.

Further, according to a fourteenth aspect of the present invention, there is provided an optical image measuring method according to the thirteenth aspect, characterized in that: the intensity modulating step includes modulating the intensity of the superimposed light while changing the modulation frequency; the detection step includes receiving a plurality of superimposed light beams whose intensity is modulated at different modulation frequencies changed by the second modulation frequency changing means and outputting a plurality of detection signals, each of which includes the interference frequency components; and the image forming step includes: forming a plurality of two-dimensional images, each of which is based on an interference frequency component corresponding to a beat frequency substantially equal to a modulation frequency at which an intensity of a superimposed light beam is modulated in the intensity modulating step, in accordance with each of the plurality of outputted detection signals; and synthesizing the plurality of formed two-dimensional images with one another to form a two-dimensional velocity distribution image.

Further, according to a fifteenth aspect of the present invention, there is provided an optical image measuring method according to any one of the eleventh to fourteenth aspects, characterized by further including an optical path length changing step for changing an optical path length of the reference light to change a measurement depth of the object to be measured, and characterized in that: the detection step includes outputting a plurality of detection signals corresponding to a plurality of measurement depths which are different from one another based on optical path lengths of the reference light; and the image forming step includes: forming a plurality of two-dimensional velocity distribution images corresponding to the measurement depths based on the outputted detection signals corresponding to the plurality of measurement depths; and arranging the plurality of formed two-dimensional velocity distribution images in a measurement depth direction and performing image processing on the arranged two-dimensional velocity distribution images to form a three-dimensional velocity distribution image.

Further, according to a sixteenth aspect of the present invention, there is provided an optical image measuring method according to any one of the eleventh to fifteenth aspects, characterized by further including a display step for displaying the velocity distribution images formed in the image forming step.

Further, according to a seventeenth aspect of the present invention, there is provided an optical image measuring method according to any one of the eleventh to sixteenth aspects, characterized in that the object to be measured comprises at least one of a retina of an eye to be examined and a lower tissue of the retina; and the moving matter comprises one of blood flowing through a blood vessel of at least one of the retina and the lower tissue of the retina and blood containing a contrast agent injected in advance.

According to the first or eleventh aspect of the present invention, the low-coherent light beam whose intensity is periodically modulated at the modulation frequency is outputted, the beam diameter of the outputted light beam is increased, the polarization characteristic of the light beam is converted to linear polarization, the light beam is divided into signal light propagating to an object to be measured and reference light propagating to the reference object, the polarization characteristic of one of the signal light and the reference light, which are linearly polarized light, is converted, the signal light whose part propagating through the moving matter in the object to be measured is subjected to frequency shift and the reference light propagating through the reference object are superimposed on each other to produce. superimposed light including interference light having the beat frequency corresponding to the quantity of the frequency shift applied to the signal light, in which one of the signal light and the reference light is the linearly polarized light acquired in the first converting step and the other thereof has the further converted polarization characteristic, the plurality of different polarized light components of the interference light included in the produced superimposed light are received and the detection signal including interference frequency components corresponding to beat frequencies of the interference light is outputted, and the velocity distribution image expressing the moving velocity distribution of the moving matter is formed based on an interference frequency component corresponding to the beat frequency substantially equal to the modulation frequency at which the intensity of the light beam is modulated by the light beam outputting step, among the interference frequency components included in the outputted detection signal. Therefore, a two-dimensional image can be acquired at a time using the light beam whose beam diameter is increased. Thus, the object to be measured can be speedily measured over a wide range in order to measure the moving velocity distribution image of the moving matter in the object to be measured.

According to the fourth or thirteenth aspect of the present invention, the light beam which is low-coherent is outputted, the beam diameter of the outputted light beam is increased, the light beam whose beam diameter is increased is divided into signal light propagating to an object to be measured and reference light propagating to the reference object, the signal light whose part propagating through the moving matter in the object to be measured is subjected to frequency shift and the reference light propagating through the reference object are superimposed on each other to produce superimposed light including interference light having the beat frequency corresponding to the quantity of the frequency shift, an intensity of the produced superimposed light is periodically modulated, the superimposed light whose intensity is modulated is received and the detection signal including interference frequency components corresponding to beat frequencies of the interference light is outputted, and the velocity distribution image expressing the moving velocity distribution of the moving matter is formed based on an interference frequency component corresponding to the beat frequency substantially equal to the modulation frequency at which the intensity of the superimposed light is modulated by the intensity modulating step, among the interference frequency components included in the outputted detection signal. Therefore, a two-dimensional image can be acquired at a time using the light beam whose beam diameter is increased. Thus, the object to be measured can be speedily measured over a wide range in order to measure the moving velocity distribution image of the moving matter in the object to be measured.

According to the present invention, the measurement is performed using the light beam whose beam diameter is increased, so it is unnecessary to perform scanning while the object to be measured is moved in directions (x-y directions) orthogonal to the propagating direction of the signal light. Even when the object to be measured is the living tissue, it is possible to effectively measure the object to be measured over a wide range in order to measure the velocity distribution image expressing a distribution such as a flow velocity distribution of blood flowing through the blood vessel of the living tissue.

According to the seventh or fifteenth aspect of the present invention, the optical path length of the reference light can be changed to change the measurement depth of the object to be measured. Therefore, it is unnecessary to move the object to be measured even in the case of scanning in the measurement depth direction (z-direction). Thus, it is possible to more preferably measure the velocity distribution image of the living tissue.

BRIEF DESCRIPTION OF THE DRAWINGS

In the accompanying drawings:

FIGS. 6A to 6E are explanatory graphs showing interference light detection modes of the optical image measuring apparatus according to the first embodiment of the present invention, in which FIG. 6A illustrates a temporal waveform of a light beam whose intensity is modulated at a frequency and which is outputted from a broad-band light source, FIG. 6B illustrates a temporal waveform of an S-polarized light component of interference light in the case where the light beam outputted from the broad-band light source is continuous light, FIG. 6C illustrates a temporal waveform of a P-polarized light component of the interference light in the case where the light beam outputted from the broad-band light source is continuous light, FIG. 6D illustrates a temporal waveform of the S-polarized light component of the interference light in the case where the intensity of the light beam outputted from the broad-band light source is modulated, and FIG. 6E illustrates a temporal waveform of the P-polarized light component of the interference light in the case where the intensity of the light beam outputted from the broad-band light source is modulated;

DETAILED DESCRIPTION OF THE PREFERRED EMBODIMENTS

Examples of an optical image measuring apparatus and an optical image measuring method according to each of preferred embodiments of the present invention will be described in detail with reference to the accompanying drawings.

The present invention is utilized to form a two-dimensional image such as a tomographic image or a surface image of an object to be measured, for example, in the medical field and the industrial field and a three dimensional image of the object to be measured. The object to be measured in the present invention includes a living tissue composed of a scattering medium, such as a human eye, for example, in the medical field. The present invention includes a structure for forming an image expressing a moving velocity (such as a blood flow velocity) of a moving matter such as blood flowing through a blood vessel of a living tissue (such as a retina or a lower tissue thereof) when the moving matter exists in the object to be measured.

In the present invention, the "moving matter" indicates an arbitrary measurement subject moving in the object to be measured. The moving matter may be in an arbitrary state such as a solid state, a liquid state, a gas state, or a gel state.

Firsr Embodiment

A first embodiment of the present invention will be described. In this embodiment, a plurality of polarized light components included in interference light having information related to the object to be measured are detected to form an image of the object to be measured.

[Structure of Apparatus]

Figure 1:
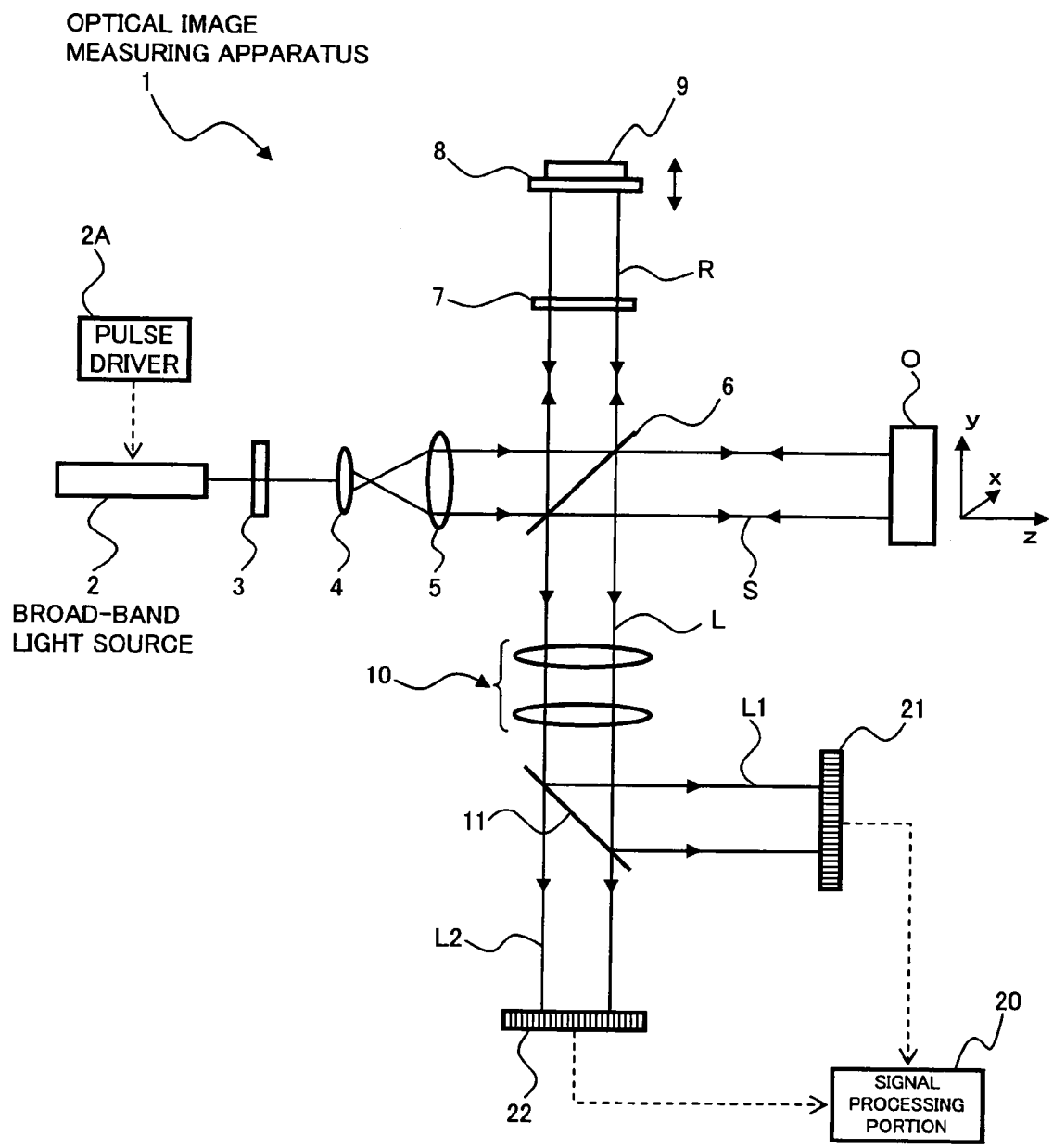
FIG. 1 is a schematic diagram showing an example of an optical image measuring apparatus according to a first embodiment of the present invention.
Figure 2:
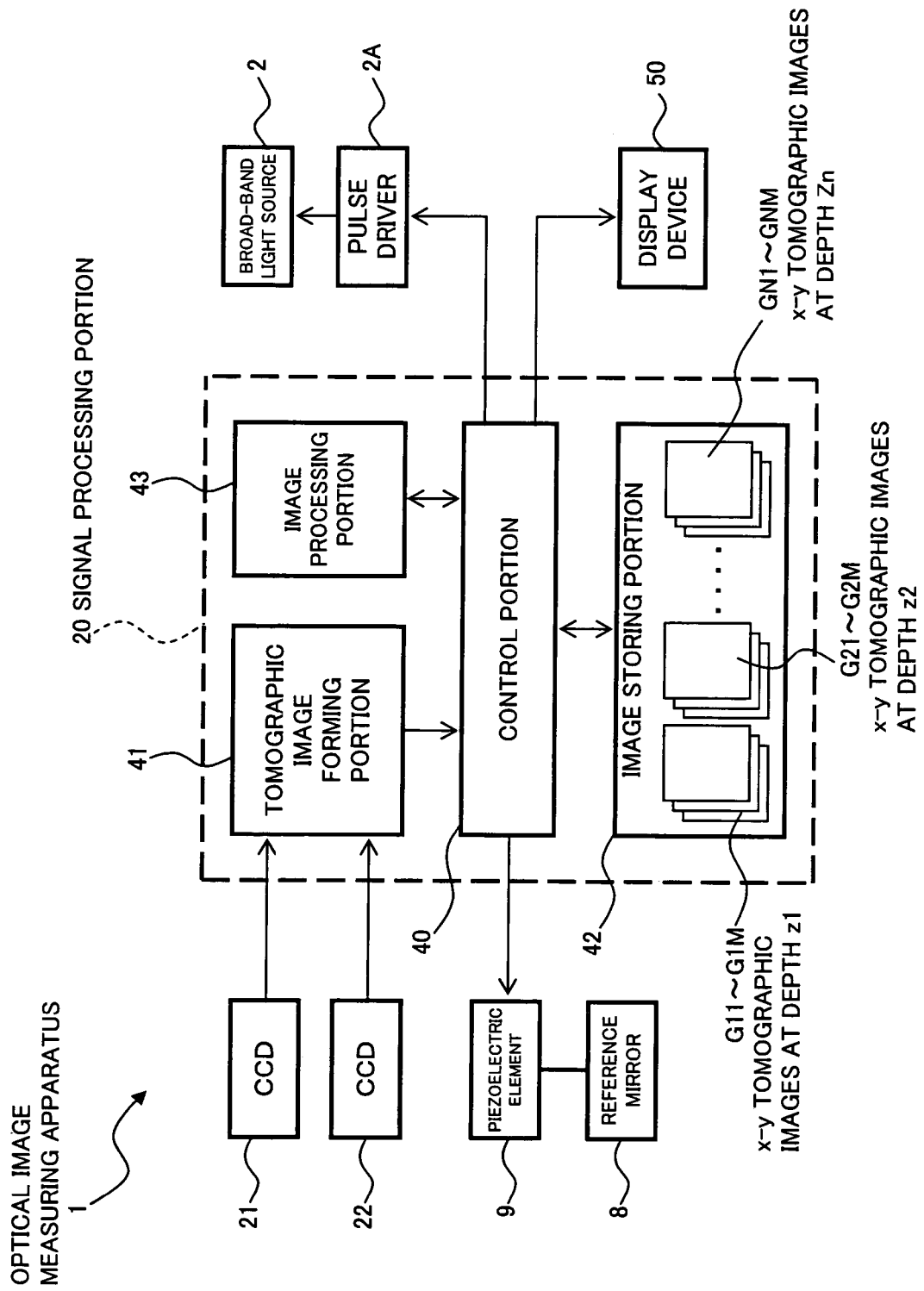
FIG. 2 is a block diagram showing an example of a control system of the optical image measuring apparatus according to the first embodiment of the present invention.

An optical image measuring apparatus according to the first embodiment of the present invention will be described with reference to FIGS. 1 and 2. FIG. 1 illustrates a schematic structure of an optical system of the optical image measuring apparatus according to this embodiment and FIG. 2 illustrates a structure of a control system thereof.

[Structure of Optical System]

First, the optical system of the optical image measuring apparatus according to this embodiment will be described with reference to FIG. 1. The optical image measuring apparatus 1 shown in FIG. 1 includes a broad-band light source 2 for outputting a low-coherent light beam, a polarizing plate 3 for converting a polarization characteristic of the light beam to linear polarization, lenses 4 and 5 for converting the light beam to a parallel light flux and increasing a beam diameter thereof, which compose "increasing means" in the present invention, and a half mirror 6 for dividing the light beam into signal light S and reference light R and superimposing the signal light S and the reference light R on each other to produce superimposed light L. The optical image measuring apparatus 1 further includes a wavelength plate 7 for converting a polarization characteristic of the reference light R from linear polarization to circular polarization, a reference mirror 8 for totally reflecting the reference light R on a reflective surface orthogonal to a propagating direction of the reference light R, and a piezoelectric element 9 provided on a rear surface opposite to the reflective surface of the reference mirror 8.

The broad-band light source 2 is composed of an SLD, a light-emitting diode (LED), or the like. A coherent length of an available near-infrared region SLD is about 30 µm and a coherent length of an LED is about 10 µm. The broad-band light source 2 is driven based on a pulse signal having a predetermined frequency which is outputted from a pulse driver 2A to periodically output a pulse light beam (this will be described in detail later). At this time, the light beam from the broad-band light source 2 is outputted as, for example, pulse light of a rectangular train with a duty of 50%. The broad-band light source 2 and the pulse driver 2A compose "light beam outputting means" in the present invention.

In an xyz-coordinate system shown in FIG. 1, a propagating direction of the light beam outputted from the broad-band light source 2 is defined as a z-direction and an oscillation plane of the light beam orthogonal to the propagating direction thereof is defined as an x-y plane. The x-direction and a y-direction are defined so as to align with an oscillation plate of an electric field component of the light beam and an oscillation plate of a magnetic field component thereof, respectively. The z-direction is defined as a propagating direction of the signal light S propagating to an object to be measured O, and also as a measurement depth direction of the object to be measured O.

The polarizing plate 3 corresponds to the "first converting means" in the present invention and is a polarization conversion element for transmitting an oscillation component of the light beam in a predetermined direction, which is outputted from the broad-band light source 2. In this embodiment, the polarizing plate 3 is constructed to transmit an oscillation component in an angle direction by 45° with respect to an x-axis (and a y-axis) of the xy-plane. The light beam passing through the polarizing plate 3 has linearly polarized light by 45°. Therefore, the amplitudes of polarization components of the light beam in the x-axis direction and the y-axis direction are equal to each other. In other words, the amplitude of a P-polarized light component of the light beam is equal to that of a S-polarized light component thereof.

The half mirror 6 composes the "dividing means" in present invention, for dividing the linearly polarized, parallel beam into the signal light S propagating to the object to be measured O and the reference light R propagating to the reference mirror 8. The half mirror 6 transmits a part (half) of the light beam as the signal light S and reflects the rest thereof as the reference light R.

The half mirror 6 further composes "superimposing means" in the present invention and acts to reflect a part of the signal light S propagating through the object to be measured O and transmit a part of the reference light R propagating through the reference mirror 8 to superimpose the signal light S and the reference light R, thereby producing the superimposed light L. The superimposed light L is pulse light having a frequency equal to that of the light beam outputted from the broad-band light source 2.

In this embodiment, because a Michelson interferometer is used, the dividing means and the superimposing means each are composed of (different reflective surface of) the same half mirror 6. On the other hand, when another type of interferometer such as a Mach-Zehnder interferometer is employed, an optical element composing the dividing means may be different from that composing the superimposing means. An arbitrary non-polarization beam splitter having no influence on the polarization characteristics of the light beams (signal light S and reference light R) is preferably applied to each of the dividing means and the superimposing means.

The wavelength plate 7 composes a "second converting means" in the present invention and is a polarization conversion element for converting the polarization characteristic of the reference light R which is converted to the linear polarization by the polarizing plate 3. In this embodiment, a ⅛-wavelength plate is used as the wavelength plate 7. Therefore, when the reference light R passes through the wavelength plate 7, a phase difference of $\pi/4$ is provided between a P-polarized light component of the reference light R and an S-polarized light component thereof. In each of the case where the reference light R propagates from the half mirror 6 to the reference mirror 9 and the case where the reference light R is reflected on the reference mirror 8 and incident on the half mirror 6 again, the above-mentioned phase difference is applied to the reference light R. As a result, a phase difference of $\pi/2$ is applied to the reference light R. Thus, the wavelength plate 7 acts on the reference light R having linearly polarized light of 45° in the same manner as the ¼-wavelength plate, so the reference light R which is incident on the half mirror 6 again is converted to circularly polarized light. When another interferometer such as the Mach-Zehnder interferometer is used as described above, it is possible to apply the ¼-wavelength plate.

The reference mirror 8 composes a "reference object" in the present invention. The reference mirror 8 is moved in the optical path direction of the reference light R by the piezoelectric element 9 to extract reflection light of the signal light S from the object to be measured O at each depth (z-coordinate) thereof. More specifically, because the light beam from the broad-band light source 2 is the low-coherent light, only the signal light S propagating a distance substantially equal to a propagating distance of the reference light R is useful to produce interference light included in the superimposed light L. In other words, only reflection light on a z-coordinate region of the object to be measured O which is located at a distance substantially equal to a distance to the reference mirror 8 relative to the half mirror 6 interferes with the reference light R to cause a beat frequency. Therefore, the reference mirror 8 is moved (subjected to z-scanning) to change an optical path length of the reference light R. Thus, it is possible to subsequently detect reflection light on each z-coordinate region of the object to be measured O. The reference mirror 8 and the piezoelectric element 9 compose "optical path length changing means" in the present invention.

The reference mirror 8 is vibrated by the piezoelectric element 9 in the optical path direction of the reference light R. Therefore, the reference light R is subjected to frequency shift. At this time, the reference mirror 8 and the piezoelectric element 9 compose "frequency shifting means" in the present invention.

The superimposed light L will be described. The superimposed light L is produced by superimposing the signal light S and the reference light R on each other. Only the signal light S will be described because the reference light R is described above. Assume that the object to be measured O is the retina (fundus) of a human eye. Note that the object to be measured O is not limited to the retina of the human eye and thus may be the retina of an eye of an arbitrary animal. Such an eye subjected to an examination is generically referred to as an "eye to be examined".

Figure 11:
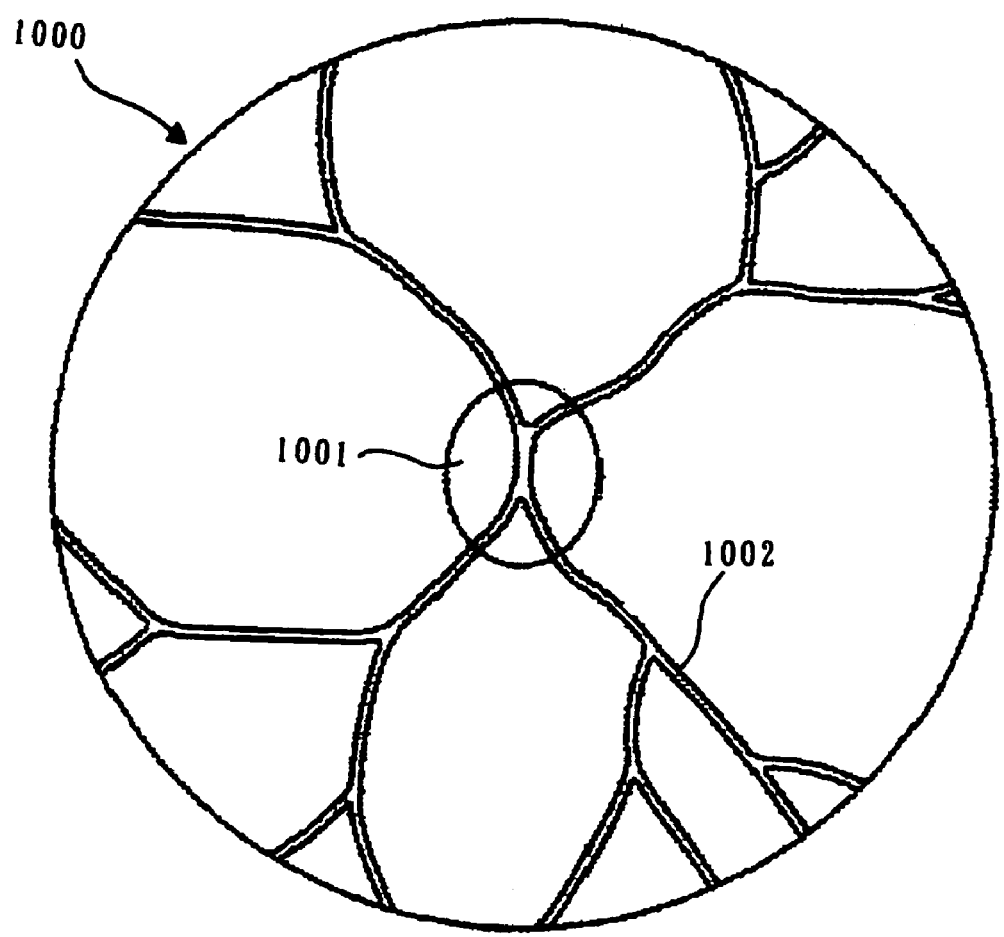
FIG. 11 is a schematic view showing a shape of a retina of an eye to be examined.

FIG. 11 illustrates a schematic form of a retina. A retina 1000 includes a blood vessel 1002 passing through an optic papilla 1001, such as a retinal artery or a retinal vein. Blood (moving matter) flows through the blood vessel 1002. The blood vessel 1002 is formed in a shape such that it three-dimensionally winds in the retina 1000. A flow direction of blood is three-dimensional. Therefore, a blood flow velocity at an arbitrary position of the blood vessel 1002 is expressed by a three-dimensional vector.

Figure 12:
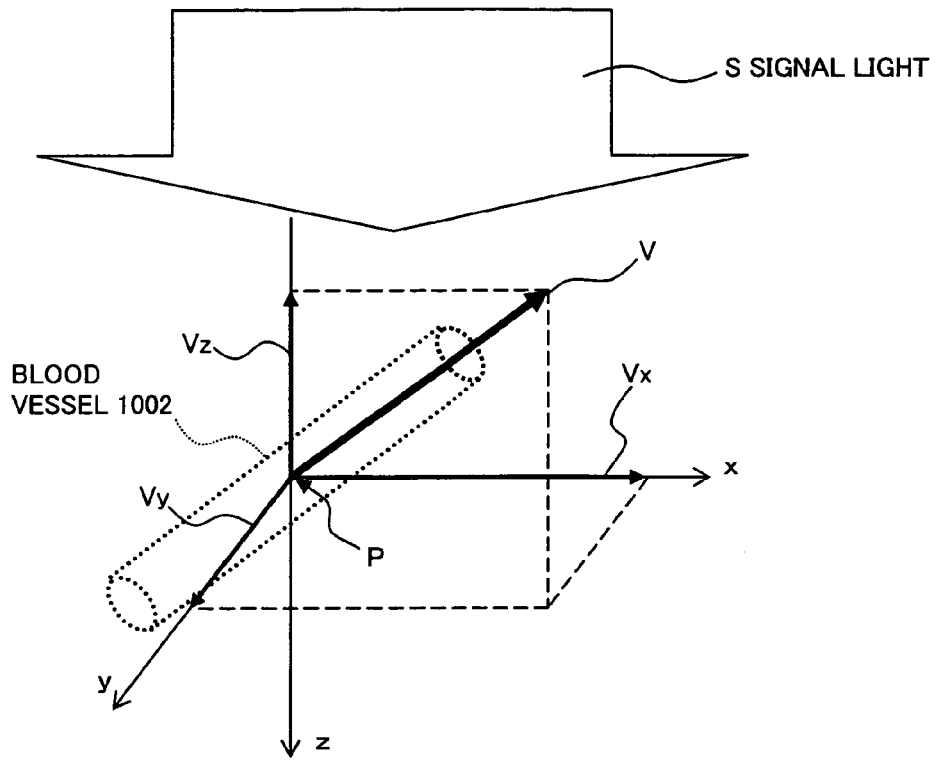
FIG. 12 is a schematic view showing a blood flow state of a blood vessel at an arbitrary position of the retina of the eye to be examined and an incident state of the signal light at the arbitrary position.

FIG. 12 illustrates the flow of blood at an arbitrary position P of the blood vessel 1002. In FIG. 12, assume that the signal light S is incident on the blood vessel 1002 from above and the z-direction of the xyz-coordinate system is set to a downward direction (that is, the half mirror 6 is located upward). The blood flow velocity (moving velocity of the moving matter) at the position P of the blood vessel 1002 is expressed by V which denotes the three-dimensional vector. Respective x-, y-, and z-components of the blood flow velocity V are expressed by $V_x$, $V_y$, and $V_z$.

At this time, the signal light S is incident on the blood vessel 1002 in a minus-z-direction, so the signal light is influenced by the z-component $V_z$ of the blood flow velocity V. That is, the signal light S reflected at the position P of the blood vessel 1002 is subjected to frequency shift by the Doppler effect due to blood flow. The amount of frequency shift at the position P depends on the z-component $V_z$ of the blood flow velocity V. Because the beam diameter of the signal light S is increased by the lenses 4 and 5, only a part of the signal light S passing through the position P is subjected to the frequency shift.

As described above, the part of the signal light S passing through the arbitrary position of the blood vessel 1002 is subjected to the frequency shift based on the z-component of the blood flow velocity at the position. Therefore, the signal light S exiting from the object to be measured O normally includes a plurality of frequency components corresponding to different positions of the blood vessel 1002.

From the above description, the superimposed light L includes interference light having a beat frequency corresponding to a difference between frequency shift to which the reference light R is subjected by the movement of the reference mirror 8 and frequency shift to which the signal light S is subjected by the flow of blood flowing through the blood vessel 1002. Therefore, the superimposed light L includes a plurality of interference light beams having different beat frequencies, corresponding to a plurality of parts of the signal light S passing through different positions of the blood vessel 1002. A beat frequency component of each of the interference light beams corresponds to the amount of frequency shift which is applied by the blood flow to the part of the signal light S. When the z-components of the blood flow velocities in different positions of the blood vessel 1002 are equal to each other, interference light beams produced corresponding to the positions have beat frequencies equal to each other.

Return to the description of the optical image measuring apparatus 1 according to this embodiment. The optical image measuring apparatus 1 further includes an imaging lens group 10 for imaging the superimposed light L produced by the half mirror 6, a polarization beam splitter 11 for dividing an optical path of the superimposed light L into two, CCDs (cameras) 21 and 22 provided on the two optical paths of the superimposed light L, and a signal processing portion 20 for processing results obtained by detection with the CCDs 21 and 22.

The polarization beam splitter 11 acts to separate the plurality of different polarized light components of an interference light beam included in the superimposed light from each other. More specifically, the polarization beam splitter 11 acts to reflect a part of the superimposed light L (referred to as superimposed light beam L1) including the S-polarized light component of the interference light beam to guide the superimposed light beam L1 to the CCD 21 and to transmit a part of the superimposed light L (referred to as superimposed light beam L2) including the P-polarized light component of the interference light beam to guide the superimposed light beam L2 to the CCD 22. As described above, the amplitude of the S-polarized light component of the interference light beam is equal to that of the P-polarized light component thereof in a configuration (45°) of the polarization axis of the polarizing plate 3.

The CCDs 21 and 22 compose "two-dimensional photo detection means" in the present invention and each are a storage type two-dimensional photo sensor array for interference light detection. The CCD 21 receives the superimposed light beam L1 reflected on the polarization beam splitter 11, performs photoelectric conversion thereon to generate a detection signal, and outputs the detection signal to the signal processing portion 20. The superimposed light beam L1 received by the CCD 21 includes the S-polarized light component of the interference light beam. Similarly, the CCD 22 receives the superimposed light beam L2 passing through the polarization beam splitter 11, performs photoelectric conversion thereon to generate a detection signal, and outputs the detection signal to the signal processing portion 20. The superimposed light beam L2 received by the CCD 22 includes the P-polarized light component of the interference light beam.

As described above, the superimposed light L (each of superimposed light beams L1 and L2) includes the plurality of interference light beams having the difference beat frequencies. Therefore, each of the detection signals outputted from the CCDs. 21 and 22 includes the beat frequency components of the plurality of interference light beams ("interference frequency components" in the present invention). A frequency of each of the interference frequency components is equal to the beat frequency of a corresponding interference light beam.

The signal processing portion 20 executes calculation processing described later based on the detection signals outputted from the CCDs 21 and 22. The signal processing portion 20 analyzes a result obtained by the calculation processing to form a two-dimensional (tomographic) image of the object to be measured O. The two-dimensional tomographic image formed by the signal processing portion 20 is an x-y tomographic image of the object to be measured O at a depth (z-coordinate) in which a length of the optical path of the signal light S becomes substantially equal to that of the optical path of the reference light R. Therefore, according to the optical image measuring apparatus 1, it is possible to acquire the x-y tomographic image of the object to be measured O in an arbitrary depth region by one-time measurement (that is, without scanning in x-y directions).

Although will be described in detail later, the signal processing portion 20 forms various images such as a three-dimensional image of the object to be measured O, a two-dimensional tomographic image thereof (x-z tomographic image or y-z tomographic image) in the measurement depth direction (z-direction), and a two-dimensional tomographic image thereof in an arbitrary direction oblique to at least one of an x-axis, an y-axis, and an z-axis based on the x-y tomographic images acquired at various depths.

The signal processing portion 20 performs image forming processing for forming an image expressing a distribution of a moving velocity of a moving matter in the object to be measured O, such as a distribution of a flow velocity of blood in a retina (referred to as a "velocity distribution image") based on the detection signals outputted from the CCDs 21 and 22. A change in the moving velocity of the moving matter on the velocity distribution image is expressed with color, gradation, and the like. The image forming processing will be described in detail later.

The signal processing portion 20 executing the above-mentioned processings composes "image forming means" in the present invention and is composed of, for example, a computer which includes a storage device storing a predetermined program, such as a ROM or a hard disk drive and a calculation control device executing the program, such as a CPU. The structure and the operation of the signal processing portion 20 will be described in detail later. The images formed by the signal processing portion 20 is displayed on a display device such as a monitor device (not shown).

The tomographic image measurement principle based on the above-mentioned structure will be described later.

[Structure of Control System]

Next, the control system of the optical image measuring apparatus 1 will be described with reference to the block diagram shown in FIG. 2. The control system of the optical image measuring apparatus 1 includes the signal processing portion 20, the CCDs 21 and 22, the pulse driver 2A (and the broad-band light source), the piezoelectric element 9 (and the reference mirror 8), and a display device 50. The display device 50 corresponds to an example of "display means" in the present invention.

The signal processing portion 20 is composed of the above-mentioned computer or the like and includes a control portion 40, a tomographic image forming portion 41, an image storing portion 42, and an image processing portion 43.

(Control Portion)

The control portion 40 controls calculation processing, image processing, and operation control processing, which are executed by the signal processing portion 20 and is composed of a CPU and the like. In particular, the control portion 40 composes a "first modulation frequency changing means" in the present invention, for controlling the pulse driver 2A to change a frequency at which the light beam is outputted from the broad-band light source 2. The control portion 40 controls the piezoelectric element 9 to control the movement or the vibration of the reference mirror 8 in the optical path of the reference light R. The control portion 40 performs processing for measuring the object to be measured O and causing the display device 50 to display an acquired image, an operation screen, or the like.

(Tomographic Image Forming Portion)

The tomographic image forming portion 41 executes calculation processing as described in detail in [Measurement Principle] (mentioned later) to form an x-y tomographic image (two-dimensional image) of the object to be measured O based on the detection signals outputted from the CCDs 21 and 22.

As described above, each of the detection signals from the CCDs 21 and 22 includes the plurality of interference frequency components corresponding to the various interference light beams having beat frequencies. The superimposed light beams L1 and L2 are detected by the CCDs 21 and 22 as pulse light beams each having a frequency equal to that of the light beam form the broad-band light source 2. The tomographic image forming portion 41 forms the x-y tomographic image based on an interference frequency component corresponding to a beat frequency (substantially) equal to the frequency of the pulsed superimposed light beams L1 and L2 (that is, the frequency at which the light beam is outputted from the broad-band light source 2), of the plurality of interference frequency components included in each of the detection signals.

Therefore, the x-y tomographic image formed by the tomographic image forming portion 41 becomes an image expressing a distribution of the interference light beam having the beat frequency, that is, a distribution (position) of a moving matter having the z-component of a predetermined moving velocity.

The detection signals corresponding to each of the pulsed light beams periodically outputted from the broad-band light source 2 are subsequently inputted from the CCDs 21 and 22 to the tomographic image forming portion 41. The tomographic image forming portion 41 executes image forming processing based on the subsequently inputted detection signals to subsequently form x-y tomographic images.

Assume that the number of x-y tomographic images to be measured in the measurement depth direction, that is, the number of scans (slices) in the z-direction is expressed by N and a measurement depth of each of slices is expressed by $z_i$ (i=1 to N). In the z-coordinate, $z_i < z(i+1)$ is assumed. Assume that the number of x-y tomographic images to be measured (the number of measurement operations) at each measurement depth zi is expressed by M. In this time, an output frequency of the light beam outputted as pulsed light is changed (this will be described in detail later). Therefore, in this embodiment, the measurement operation is firstly performed M-times at a depth z1 while the output frequency of the light beam is changed. Then, the measurement operation is performed M-times at a depth z2 while the output frequency of the light beam is changed. The same measurement operations are subsequently performed. Finally, the measurement operation is performed M-times at a depth zN while the output frequency of the light beam is changed.

The measurement operations are realized by the control of the control portion 40. The tomographic image forming portion 41 forms (M×N) x-y tomographic images Gij (i=1 to N and j=1 to M) based on the detection signals corresponding to each of the measurement operations of (M×N) times in total. The formed images Gij are stored in the image storing portion 42 by the control portion 40.

(Image Storing Portion)

The image storing portion 42 is used to store the x-y tomographic images Gij formed by the tomographic image forming portion 41 and composed of a storage device such as an image memory or a hard disk drive. Directories are allocated to information stored in the image storing portion 42. The directories are associated with one another to associate the stored information with one another. The x-y tomographic images Gij are associated with one another for each measurement depth zi. In other words, images G11 to G1M at the depth z1 are firstly associated with one another. Images G21 to G2M at the depth z2 are associated with one another. Then, the same association is successively performed. Finally, images GN1 to GNM at the depth zN are associated with one another. Therefore, the x-y tomographic images Gij are stored in the image storing portion 42 based on such associations. The storage processing and association processing on the image storing portion 42 are performed by the control portion 40.

(Image Processing Portion)

The image processing portion 43 forms a velocity distribution image based on the x-y tomographic images Gij (i=1 to N and j=1 to M) formed by the tomographic image forming portion 41. The formed velocity distribution image is, for example, a two-dimensional image expressing a velocity distribution of a moving matter in a two-dimensional region at the depth zi, which is formed based on M x-y tomographic images Gi1 to GiM or a three-dimensional image expressing the velocity distribution of the moving matter in a three-dimensional region at the depths z1 to ZN, which is formed based on (M×N) x-y tomographic images G11 to GNM. Such processing performed by the image processing portion 43 will be described in detail later.

Each of the x-y tomographic images Gi1 to GiM is an image expressing a distribution of moving matters whose moving velocities are equal to one another in the two dimensional region at the depth zi. The x-y tomographic images express distributions of moving matters having different moving velocities. Therefore, a velocity distribution image formed by the image processing portion 43 expresses the position of the moving matter in the two dimensional region at the depth zi so as to be able to recognize the moving velocity thereof. The moving velocity of the moving matter is expressed with color and gradation.

The velocity distribution image formed by the image processing portion 43 is displayed on the display device 50 by the control portion 40. The formed velocity distribution image may be stored in the image storing portion 42 or the like.

[Measurement Processing]

An example of image measurement processing of the object to be measured O which is performed by the optical image measuring apparatus 1 having the above-mentioned structure will be described. Hereinafter, the flow of the image measurement processing will be described and then the measurement principle thereof will be described.

[Flow of Measurement Processing]

Figure 3:
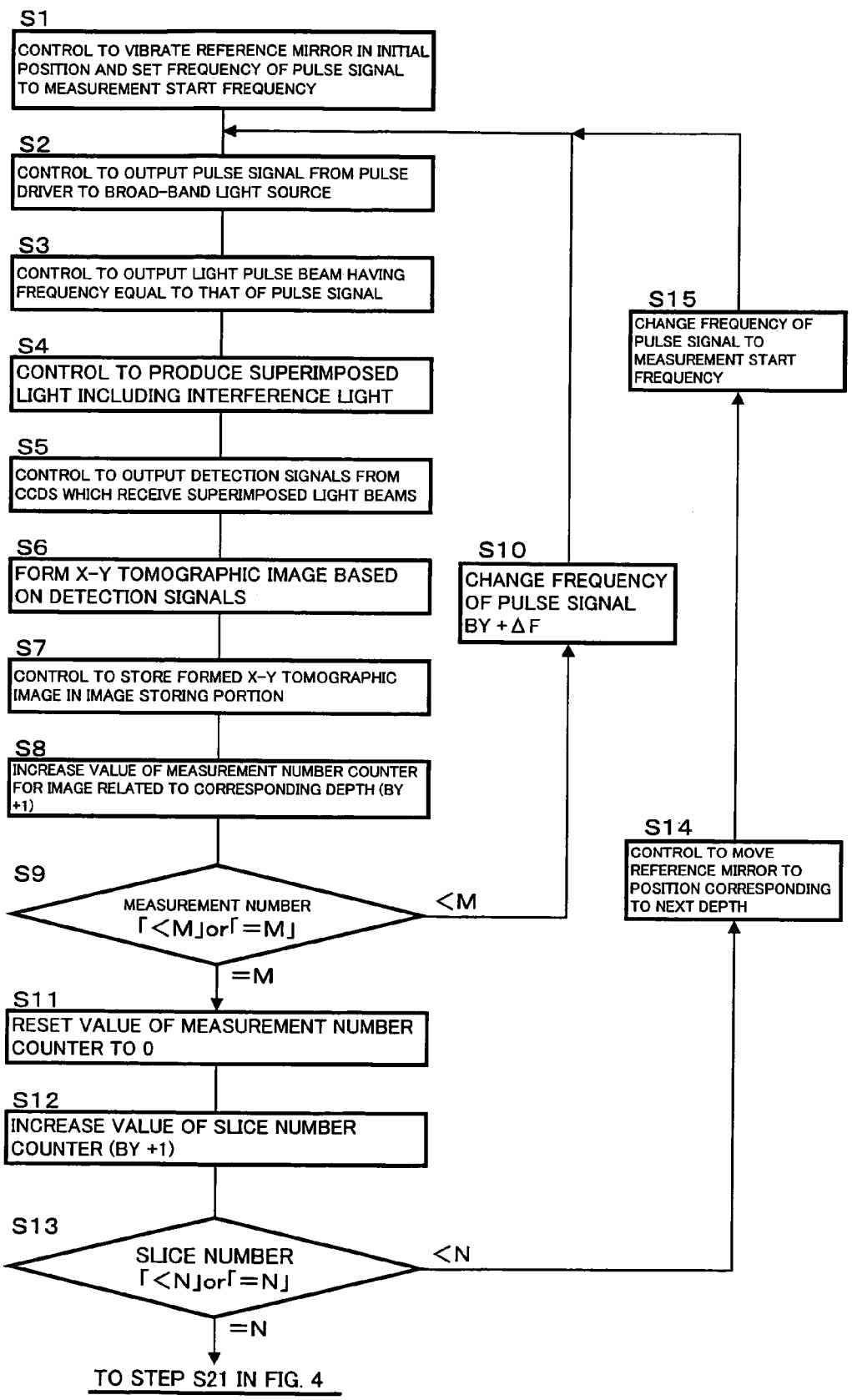
FIG. 3 is a flow chart showing an example of measurement processing executed by the optical image measuring apparatus according to the first embodiment of the present invention.
Figure 4:
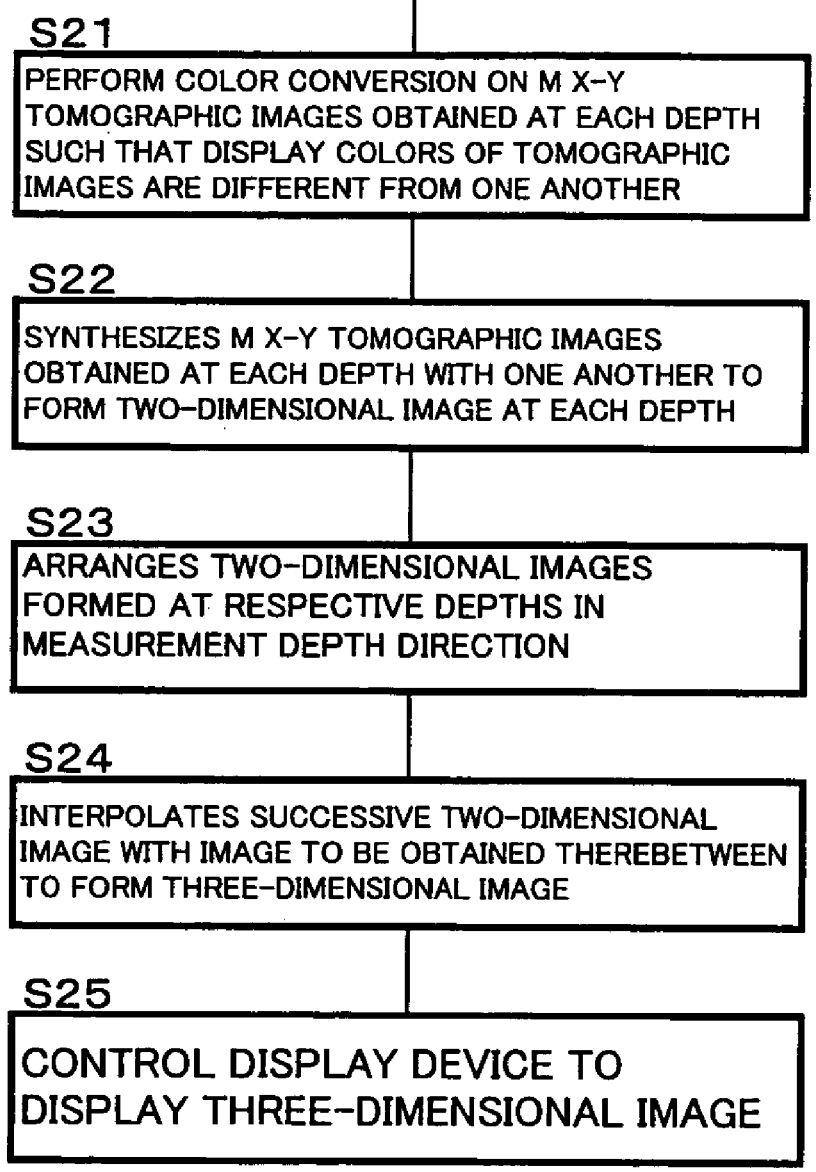
FIG. 4 is a flow chart showing an example of the measurement processing executed by the optical image measuring apparatus according to the first embodiment of the present invention.

FIGS. 3 and 4 are flow charts showing an example of the measurement processing performed by the optical image measuring apparatus 1. FIG. 3 illustrates an example of a procedure for acquiring a tomographic image of the object to be measured O. FIG. 4 illustrates an example of a procedure for forming a three-dimensional image of the object to be measured O based on the acquired tomographic image.

(Tomographic Image Acquisition Processing: FIG. 3)

First, the processing procedure for acquiring the tomographic image will be described with reference to the flow chart shown in FIG. 3.

Assume that the number of scans (slices) in the z-direction (N) and the number of measurement operations (M) in each of the slices, that is, at each depth zi (i=1 to N) are set in advance.

The number of slices (N) is set based on, for example, a slice thickness (that is, a distance d $(=|z(i+1)-zi|)$) and a thickness of a measurement target region of the object to be measured O. For example, when the slice thickness which is arbitrarily set is expressed by d and the thickness of the measurement target region is expressed by D, the number of slices (N) becomes ([D/d]+1). Here, [•] denotes a Gauss symbol (function for converting a value shown in parentheses to a maximum integer which does not exceed the value). The thickness D of the measurement target region. The thickness D of the measurement target region is divided into N to determine the slice thickness.

The number of measurement operations (M) at each depth may be a predetermined default value or arbitrarily set (for example, M=100). The slice thickness d, the number of slices (N) (or thickness of the measurement target region), and the number of measurement operations (M) at each depth are set by, for example, the operation of an input device such as a keyboard or a mouse, of the computer composing the signal processing portion 20.

First, the object to be measured O at the depth z1 (for example, z=0: front surface) is measured. Under the control of the control portion 40, the reference mirror 8 is moved to a position (in an initial position) in which a distance between the half mirror 6 and the reflective surface of the reference mirror 8 is equal to a distance between the half mirror 6 and the region (x-y plane) located at the depth z1 and vibrated in the optical path direction (z-direction) of the reference light R, and the frequency of the pulse signal outputted from the pulse driver 2A is set to a predetermined frequency f0 (Step S1). The frequency f0 is referred to as a "measurement start frequency".

The pulse driver 2A outputs the pulse signal having the measurement start frequency f0 to the broad-band light source 2 under the control of the control portion 40 (Step S2). The broad-band light source 2 is driven based on the pulse signal and outputs a pulsed light beam having the frequency f0 (light pulse beam) (Step S3).

The outputted light pulse beam is converted to the linearly polarized light by the polarizing plate 3 and the beam diameter thereof is increased by the lenses 4 and 5. Then, the light pulse beam is incident on the half mirror 6 and divided into the signal light S and the reference light R. When the reference light R is reflected on the reference mirror 8, the reference light R is subjected to frequency shift. In addition to this, the reference light R passes through the wavelength plate 7 two times while it passes through the reference mirror 8 and returns to the half mirror 6, with the result that the reference light R is converted to the circularly polarized light. On the other hand, the signal light S is reflected on various depth regions of the objet to be measured O and returns to the half mirror 6. The signal light and the reference light R which return to the half mirror 6 are superimposed on each other to produce the pulsed superimposed light L (Step S4).

The superimposed light L includes interference light based on reflection light of the signal light S on a moving matter in the region of the object to be measured O at the depth z1. The beat frequency of the interference light depends on the z-component of a moving velocity of the moving matter. When a plurality of moving matters exist in the region at the depth z1, interference light corresponding to each of the moving matters is included in the superimposed light L.

The superimposed light L is divided by the polarization beam splitter 11 into the pulsed superimposed light beam L1 and the pulsed superimposed light beam L2. The superimposed light beam L1 includes the S-polarized light component of the interference light. The superimposed light beam L2 includes the P-polarized light component of the interference light. The superimposed light beam L1 and the superimposed light beam L2 are received by the CCDs 21 and 22, respectively. The CCDs 21 and 22 perform photoelectric conversion on the received superimposed light beams L1 and L2 and output the detection signals to the signal processing portion 30 (Step S5).

The tomographic image forming portion 41 forms a first x-y tomographic image G11 related to the depth z1 based on the detection signals from the CCDs 21 and 22 (Step S6). The control portion 40 sends the formed x-y tomographic image G11 to the image storing portion 42, which stores it (Step S7).

The control portion 40 counts the number of images stored in the image storing portion 42. That is, the control portion 40 increases a value of a counter (not shown) by "1" every time the image is stored (Step S8) and determines whether the value of the counter is smaller than M or equal to M ("the number of measurement operations <M" or "the number of measurement operations=M") (Step S9). As described above, "M" is the number of measurement operations performed at each depth zi set in advance. The counter for counting the number of the measurement operations is referred to as a measurement number counter.

When it is determined that the count value of the measurement number counter is smaller than M (<M), the control portion 40 controls the pulse driver 2A to change the frequency of the pulse signal to be outputted to a frequency (f0+Δf) (Step S10). Then, as in Steps S2 to S8, an x-y tomographic image G12 is formed from a result obtained by detection of the superimposed light beams L1 and L2 produced based on the light beam outputted at the frequency (f0+Δf) and stored in the image storing portion 42. The count value of the measurement number counter is increased by "1".

The same processing is repeated until the count value of the measurement number counter reaches M. Therefore, x-y tomographic images G1j corresponding to frequencies (f0+(j−1)×Δf)(j=1 to M), related to the region located at the depth z=z1 are stored in the image storing portion 42. For example, the M x-y tomographic images G11 to G1M are stored in the same folder to associate with one another.

When it is determined that the count value of the measurement number counter is equal to M (=M) (Step S9), the control portion 40 resets the count value of the measurement number counter to 0 (Step S10) and counts the number of slices (indicating the number of different measurement depths). That is, a value of a counter (not shown) is increased by 1 (Step S12). This counter is used to count the number of slices and referred to as a slice number counter.

Subsequently, the control portion 40 determines whether the count value of the slice number counter is smaller than N or equal to N (Step S13). When the count value of the slice number counter is smaller than N (<N), the control portion 40 controls to move the reference mirror 8 to a position corresponding to a next depth z=z2 (that is, a position in which the distance between the half mirror 6 and the reflective surface of the reference mirror 8 is equal to a distance between the half mirror 6 and a region located at the depth z2) (Step S14). Then, the control portion 40 changes the frequency of the pulse signal outputted from the pulse driver 2A to the measurement start frequency f0 (Step S15).

The above-mentioned processings of Step S2 to S10 related to the region located at the depth z=z2 are executed to form x-y tomographic images G2j corresponding to frequencies (f0+(j−1)×Δf) (j=1 to M). The M x-y tomographic images G21 to G2M are stored in the image storing portion 42 in association with one another.

The same processing is repeated until the count value of the slice number counter reaches N. Therefore, the x-y tomographic images Gij corresponding to the frequencies (f0+(j−1)×Δf)(j=1 to M) are acquired for each of the regions located at the depths zi (i=1 to N) set in advance. The (M×N) x-y tomographic images G11 to GNM are associated for each of the depths z1 to zN and stored in the image storing portion 42.

A change range in the frequency at which the light beam is outputted, that is, f0 to (f0+(j−1)×Δf), is set so as to have the beat frequency of the interference light beam included in the superimposed light L. When the superimposed light L includes the plurality of interference light beams having the difference beat frequencies, it is desirable to set the change range in the frequency so as to have all the beat frequencies. When attention is given on only a specific range, the change range may be set to the specific range.

(Three-dimensional Image Forming Processing: FIG. 4)

Subsequently, processing for forming a three-dimensional image of the object to be measured O based on the acquired (M×N) x-y tomographic images G11 to GNM will be described with reference to the flow chart shown in FIG. 4.

First, the image processing portion 43 performs image processing (color conversion) on M x-y tomographic images Gi1 to GiM related to the region located at each depth zi (i=1 to N) which are stored in the image storing portion 42 so that the display colors of the images are different from one another (Step S21). At this time, for example, the image processing is performed so that the color of the image becomes deeper as j (=1 to M) increases. That is, the density of each of the images Gi1 to GiM is changed as follows. For example, the color of the image Gi2 is deeper than that of the image Gi1. The color of the image Gi3 is deeper than that of the image Gi2. Then, the color of the image GiM is deeper than that of the image Gi(M−1). All the densities of the images G1j, G2j, . . . , and GNj measured in the same measurement order (j=1 to M) at the respective depths z1 to zN are converted to the same density.

The image processing in Step S21 is not limited to the above-mentioned processing for acquiring the images whose densities are different from one another. For example, color such as red, blue, or green may be changed for each of the images. It may be unnecessary to change the density and the color for each of the images. For example, the density (color) of each of the images Gi1 to Gi5 may be changed to a first density (color). The density (color) of each of the images Gi6 to Gi10 may be changed to a second density (color). Then, the density (color) of each of the images Gi(M−4) to GiM may be changed to a (M/5)-th density (color). The density or the color of each of the images Gi1 to GiM can be arbitrarily set for any purpose.

Next, the image processing portion 43 synthesizes the images Gi1 to GiM which are related to each depth zi and subjected to density conversion with one another to form the two-dimensional image Gi (i=1 to N) related to the region located at each depth zi (Step S22).

The two-dimensional image Gi is acquired by combining the image Gi1 corresponding to the frequency f0 (measurement start frequency), the image Gi2 corresponding to the frequency (f0+Δf), . . . , and the image GiM corresponding to the frequency (f0+(M−1)×Δf) with one another. The image Gij corresponding to the frequency (f0+(j−1)×Δf) (j=1 to M) is an image expressing (one or plural) positions of the moving matter in which the amount of frequency shift caused based on the z-component of the moving velocity is equal to the frequency. Therefore, the two-dimensional image Gi expresses a distribution (of z-component) of the moving velocity of the moving matter in the x-y sectional region at the coordinate (depth) zi. The densities of the respective images Gi1 to GiM are slightly different from one another, so the two-dimensional image Gi becomes a distribution image in which a change in moving velocity is expressed with gradation (gray scale).

Figure 5:
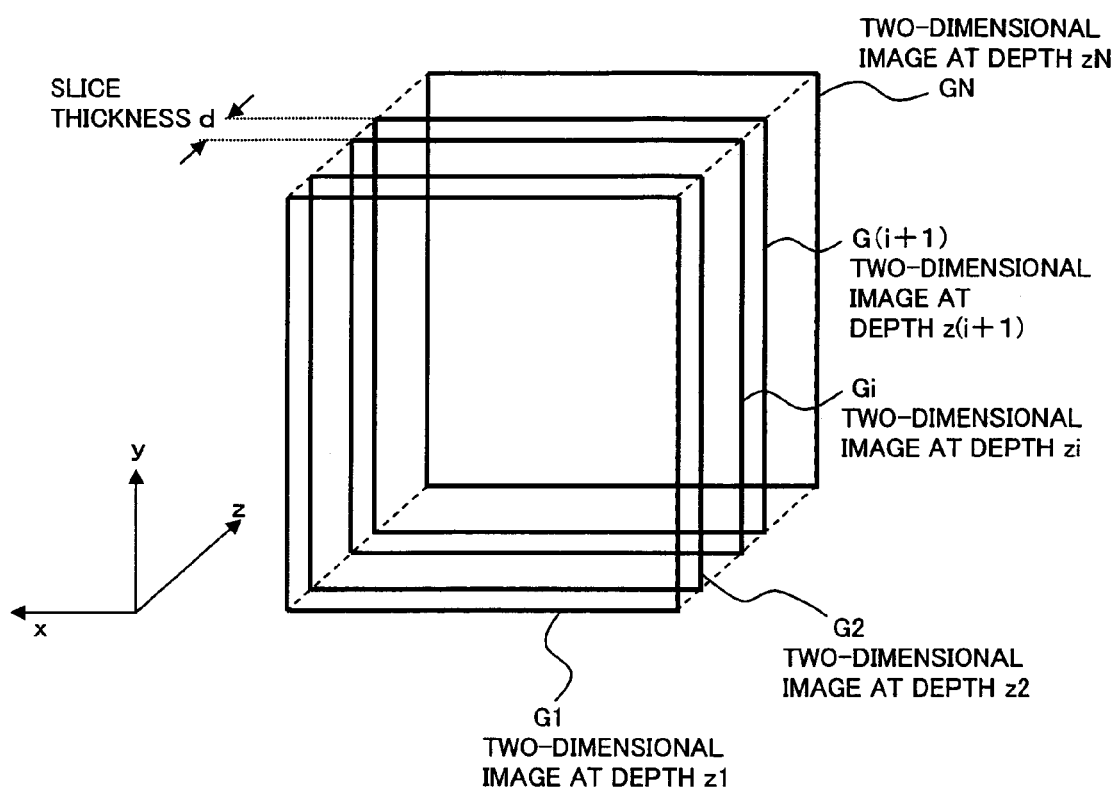
FIG. 5 is a schematic view showing an arrangement state of a plurality of two-dimensional images acquired at different measurement depths by the optical image measuring apparatus according to the first embodiment of the present invention in the case where a three-dimensional image of an object to be measured is formed based on the plurality of two-dimensional images.

Next, the image processing portion 43 arranges, in the measurement depth direction, that is, in the z-direction, the two-dimensional images G1 to GN expressing distributions of the moving velocity at the depths zi to zN (Step S23). At this time, the successive images Gi and G(i+1) are arranged at an interval corresponding to the above-mentioned slice thickness d. FIG. 5 illustrates an arrangement state of the images.

The image processing portion 43 interpolates the two-dimensional images Gi and G(i+1) (i=1 to N−1) arranged as shown in FIG. 5 with an image to be acquired therebetween to form a three-dimensional image (Step S24).

The three-dimensional image expresses a distribution of the moving velocity of the moving matter in the three-dimensional region of the object to be measured O at the depths z1 to zN. For example, when the object to be measured O is a retina and the moving matter is a blood vessel, an image expressing a three-dimensional distribution of a blood flow velocity in the retina is formed as the three-dimensional image.

The three-dimensional image formed in Step S24 is displayed on the display device 50 by the control portion 40 (Step S25). The three-dimensional image may be stored in the storage device such as the image storing portion 42. The two-dimensional images G1 to GN formed in Step S22 may be stored in the storage device.

(Other Image Forming Processing)

As described above, the three-dimensional image expressing the three-dimensional distribution of the moving velocity of the moving matter in the object to be measured O is formed. It is also possible to form another distribution image based on the two-dimensional images G1 to GN at the depths z1 to zN which are formed in Step S22.

For example, a moving velocity image in the x-z section of the object to be measured O (at an arbitrary y-coordinate y0) can be formed. In this case, the image processing portion 43 may arrange partial images (y=y0) of two-dimensional images Gi (i=1 to N) in the z-direction at the slice thickness d intervals and perform interpolation processing thereon. When a moving velocity image in the y-z section of the object to be measured O (at an arbitrary x-coordinate x0) is to be formed, the same operation is performed.

When a moving velocity distribution image in a direction oblique to the x-axis, the y-axis, or the z-axis is to be formed, for example, only a part of the three-dimensional image which intersects the oblique plane (tomographic plane) is extracted therefrom to acquire a slice image. Therefore, the moving velocity distribution can be imaged. When a distribution image in the x-z section or the y-z section is to be formed, a slice image of the three-dimensional image may be acquired in the same manner.

[Measurement Principle]

Hereinafter, the basic principle of measurement executed by the optical image measuring apparatus 1 having the structure shown in FIG. 1 will be described. The light beam outputted from the broad-band light source 2 is converted to the linearly polarized light in the angle direction of 45° relative to the x-axis by the polarizing plate 3. The beam diameter of the converted light is increased by the lenses 4 and 5 and the light whose beam diameter is increased is converted to the parallel light beam thereby. Then, the light beam is incident on the half mirror 6 and divided into the signal light S and the reference light R.

The signal light S is incident on the object to be measured O, which is made of a scattering medium, and reflected on a surface thereof and sectional surfaces at various depths. A part of the signal light S is subjected to frequency shift by the Doppler effect caused by the moving matter (such as blood) of the object to be measured O. A part of a reflection light wave from the object to be measured O is reflected on the half mirror 6 and propagates to the imaging lens group 10.

On the other hand, the reference light R passes through the (1/8) wavelength plate 7 and is reflected on the reference mirror 8 which is being vibrated by the piezoelectric element 9. Then, the reference light R passes through the wavelength plate 7 again and is incident on the half mirror 6. At this time, the polarization characteristic of the reference light R passing through the wavelength plate 7 two times is converted from the linear polarization of 45° to the circular polarization. A part of the reference light R whose polarization characteristic is converted to the circular polarization passes through the half mirror 6 and propagates to the imaging lens group 10.

At this time, a part of the signal light S whose polarization characteristic is the linear polarization and frequency is shifted and the reference light R whose polarization characteristic is converted to the circular polarization are superimposed on each other by the half mirror 6 to produce the superimposed light L including interference light. The superimposed light L propagates to the polarization beam splitter 11 through the imaging lens group 10.

The polarization beam splitter 11 acts to reflect the S-polarized light component of the interference light included in the superimposed light L and to transmit the P-polarized light component thereof. The superimposed light beam L1 including the S-polarized light component of the interference light is detected by the CCD 21 and the superimposed light beam L2 including the P-polarized light component thereof is detected by the CCD 22. The S-polarized light component of the interference light includes an S-polarized light component Ess of the signal light S and an S-polarized light component Ers of the reference light R. The P-polarized light component of the interference light includes a P-polarized light component Esp of the signal light S and a P-polarized light component Erp of the reference light R. The S-polarized light component Ess of the signal light S, the P-polarized light component Esp thereof, the S-polarized light component Ers of the reference light R, and the P-polarized light component Erp thereof each are expressed by the following expressions.

$$Ess = \sqrt{I_{ss}} \sin(2\pi(f+f_D)t+\phi) \quad (2)$$

$$Esp = \sqrt{I_{sp}} \sin(2\pi(f+f_D)t+\phi) \quad (3)$$

$$Ers = \sqrt{I_{rs}} \sin[2\pi(f+f_D')t+\phi'] \quad (4)$$

$$Erp = \sqrt{I_{rp}} \sin[2\pi(f+f_D')t+\phi'+90°] \quad (5)$$

Here, reference symbol f indicates a frequency of the light beam outputted from the broad-band light source 2. Reference symbol $f_D$ indicates the amount of frequency shift applied to the signal light S by the movement of the moving matter in the object to be measured O. Reference symbol $f_D'$ indicates the amount of frequency shift applied to the reference light R by the movement of the reference mirror 8 in the z-direction. Reference symbol $\Phi$ indicates an initial phase of the signal light S and $\Phi'$ indicates an initial phase of the reference light R. Hereinafter, assume that a difference between the amount of frequency shift caused by the reference mirror 8 and the amount of frequency shift caused by the moving matter in the object to be measured O is expressed by $\Delta f_D$ (=$f_D'-f_D$) and a difference between the initial phase of the signal light S and the initial phase of the reference light R is expressed by $\Delta\Phi$ (=$\Phi-\Phi'$). It is desirable to set the amount of frequency shift $f_D'$ caused by the reference mirror 8 so as to satisfy $f_D'>f_D$, that is, $\Delta f_D>0$. Referring to the expressions (2) to (5), the S-polarized light component of the interference light and the P-polarized light component thereof are detected by the CCDs 21 and 22 as heterodyne signals $i_1$ and $i_2$ as expressed by the following expressions.

$$i_1 \propto |E_{ss}+E_{rs}|^2 \propto I_{rs}+I_{ss}+2\sqrt{I_{rs}I_{ss}}\cos(2\pi\Delta f_D t+\Delta\phi) \quad (6)$$

$$i_2 \propto |E_{sp}+E_{rp}|^2 \propto I_{rp}+I_{sp}+2\sqrt{I_{rp}I_{sp}}\sin(2\pi\Delta f_D t+\Delta\phi) \quad (7)$$

As is apparent from the comparison between the expressions (6) and (7), a phase difference between the alternating signals of the third terms of the respective expressions is 90° because of the cosine and sine functions with the same phase. In the optical image measuring apparatus 1, in addition to utilizing such a feature, the light beams whose intensity is periodically modulated is used as measurement light to allow the realization of optical heterodyne detection without sampling processing using shutters, thereby measuring the signal intensity of the interference light L and the spatial phase distribution thereof.

Next, an interference light detection mode executed by the optical image measuring apparatus 1 will be described with reference to graphs shown in FIGS. 6A to 6E.

In a region of the object to be measured O in which the moving matter does not exist, $f_D=0$, that is, $\Delta f_D=f_D'$. Reference symbol $\Delta f_D$ indicates the difference between the amount of frequency shift caused by the reference mirror 8 and the amount of frequency shift caused by the moving matter in the object to be measured O, that is, the beat frequency of the interference light. When a modulation frequency of the intensity of the light beam outputted from the broad-band light source 2 is expressed by $f_m$, $f_m$ is changed at each step of $\Delta f$.

In view of the fact that the moving directions of the moving matter in the object to be measured O are the +z direction ($f_D>0$) and the −z direction ($f_D<0$), a frequency ($f_m=f_D'\pm k\times\Delta f$) (k=0 to m) can be set. Note that (2m+1=M (the number of measurement operations)). An image acquired when k≠0 ($f_m=f_D'$) is a normal image expressing a structure of the object to be measured O. In addition, 2m images acquired when k≠0 become images expressing the positions of the moving matter which moves at predetermined velocity in the object to be measured O.

For example, a frequency ($f_D'-m\times\Delta f$ ($f_D'+m\times\Delta f$)) is used as the measurement start frequency f0 and can be stepped up (stepped down) at each $\Delta f$ to measure M images. The measurement start frequency f0 may be set to $f_D'$ and the measurement may be performed in order of ($f_D'+\Delta f$), ($f_D'-\Delta f$), ($f_D'+2\times\Delta f$), ($f_D'-2\times\Delta f$), etc. It is desirable to satisfy $\Delta f \ll f0$ in order to improve the measurement precision.

Figure 6:
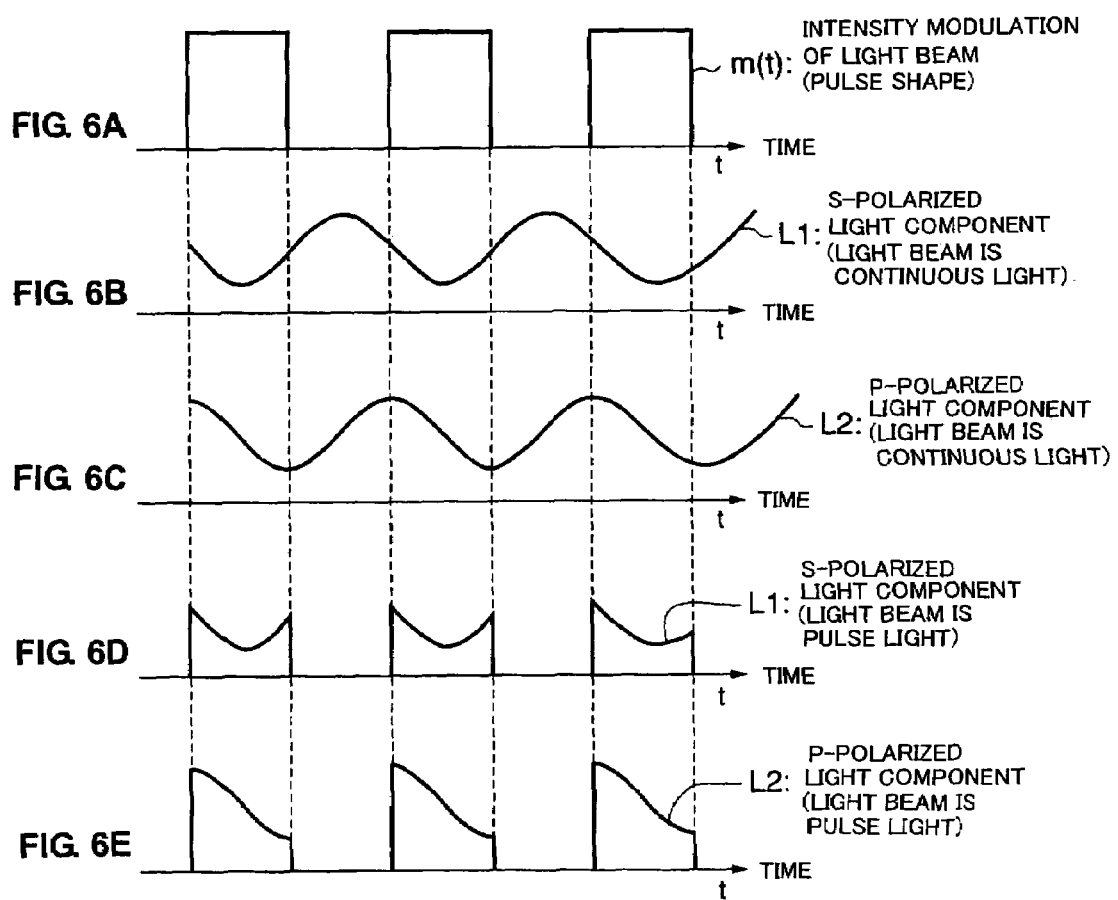

FIG. 6A illustrates a temporal waveform of a light beam which is subjected to intensity modulation at the modulation frequency $f_m$ and outputted from the broad-band light source 2. FIG. 6B illustrates a temporal waveform of the S-polarized light component of the interference light beam (beat frequency $\Delta f_D$) in the case where the light beam is continuous light and thus the reference light R and the signal light S each are continuous light. FIG. 6C illustrates a temporal waveform of the P-polarized light component of the interference light beam in the case where the reference light R and the signal light S each are continuous light. Note that a phase difference between the S-polarized light component and the P-polarized light component as shown in FIGS. 6B and 6C is 90°.

FIG. 6D illustrates a temporal waveform of the S-polarized light component of the interference light beam which is detected by the CCD 21 in the case where the modulation frequency $f_m$ of the intensity of the light beam is (substantially) equal to the beat frequency $\Delta f_D$ of the interference light beam included in the superimposed light beam L1 (this corresponds to FIG. 6B). FIG. 6E illustrates a temporal waveform of the P-polarized light component of the interference light beam which is detected by the CCD 22 in the case where the modulation frequency $f_m$ of the intensity of the light beam is (substantially) equal to the beat frequency $\Delta f_D$ of the interference light beam included in the superimposed light beam L2 (this corresponds to FIG. 6C). A phase difference between the S-polarized light component and the P-polarized light component as shown in FIGS. 6D and 6E is 90°.

The CCD 21 detects the S-polarized light component L1 having the temporal waveform shown in FIG. 6D. The light beam from the broad-band light source 2 is a light pulse of a rectangular train having the frequency $f_m$ and a duty of 50%. When a difference between the modulation frequency $f_m$ and the beat frequency $f_D$ of the interference light L ($\delta f=|f_m-f_D|$) is sufficiently smaller than a response frequency of the CCD 21 serving as the storage type photo sensor, a detection signal $S_1$ of the S-polarized light component L1 which is outputted from the CCD 21 becomes proportional to the amount of photo charge stored for a detection period. Therefore, the detection signal is expressed by the following expression (for example, see M. Akiba, K. P. Chan, and N. Tanno, Japanese Journal of Applied Physics, Vol. 39, L1194 (2000)).

$$S_1 = \langle K_1 m(t) i_1(t) \rangle \quad (8)$$

$$= K_1 \left[ \frac{1}{2} I_{ss} + \frac{1}{2} I_{rs} + \frac{2}{\pi} \sqrt{I_{ss} I_{rs}} \cos\Psi \right]$$

Here, <•> indicates a time average produced by a storage effect of the CCD 21. In addition, $K_1$ indicates photo detection efficiency including reflectance of the polarization beam splitter 11 and a photoelectric conversion rate of the CCD 21, m(t) indicates a function for modulating the output intensity of the broad-band light source 2 (function indicating a rectangular pulse), and Ψ indicates an initial phase value for measurement. As is apparent from the expression (8), the detection signal outputted from the CCD 21 includes the term related to an amplitude $\sqrt{(I_{ss} I_{rs})}$ of the S-polarized light component of the interference light in addition to the term related to the intensity of the signal light S and the term related to the intensity of the reference light R (background light component).

Similarly, the CCD 22 detects the P-polarized light component having the temporal waveform shown in FIG. 6E and outputs a detection signal $S_2$ as expressed by the following expression.

$$S_2 = K_2 \left[ \frac{1}{2} I_{sp} + \frac{1}{2} I_{rp} + \frac{2}{\pi} \sqrt{I_{sp} I_{rp}} \sin\Psi \right] \quad (9)$$

Here, $K_2$ indicates photo detection efficiency including transmittance of the polarization beam splitter 11 and a photoelectric conversion rate of the CCD 22 and Ψ indicates the initial phase value in the measurement as in the case of the expression (8).

Next, calculation processing of the signal intensity of the interference light L based on the detection signals (expressed by the expressions (8) and (9)) outputted from the CCDs 21 and 22 will be described.

Because the reference light R is converted to the circularly polarized light by the wavelength plate 7, it can be considered that an intensity $I_{rs}$ of the S-polarized light component Ers of the reference light R is equal to an intensity $I_{rp}$ of the P-polarized light component Erp thereof (this indicates $I_{rs}=I_{rp}=I_r$).

On the other hand, it is assumed that the reflection light of the signal light S on the object to be measured O does not significantly depend on the polarization characteristic of the incident light thereof, so it can be considered that an intensity $I_{ss}$ of the S-polarized light component $E_{ss}$ of the signal light S is equal to or close to the intensity $I_{sp}$ of the P-polarized light component $E_{sp}$ thereof (this indicates $I_{ss}=I_{sp}=I_s$). Because the signal light S is scattered or absorbed in the object to be measured O, it can be assumed that the intensity thereof is generally sufficiently smaller than that of the reference light R ($I_s<<I_r$).

The first term and the second term of the right side of each of the expressions (8) and (9) indicate the intensity of the background light. The intensity of the background light can be measured in advance or separately. For example, a light beam which is continuous light is outputted from the broad-band light source 2 and detected by the CCD 21 and the like. The detected light beam is integrated for a period corresponding to one wavelength (or integral multiple thereof) and the third term (alternating current component; phase quadrature component) is cancelled. Therefore, it is possible to obtain the intensity of the background light (background light component).

The obtained background light component is divided by the intensities of the detection signals from the CCDs 21 and 22 to calculate phase quadrature components of the detection signals, that is, a phase quadrature component $S_1'$ (t) of the S-polarized light component of the interference light and a phase quadrature component $S_2'$ (t) of the P-polarized light component thereof (see the following expressions).

$$S_1' = K_1 \frac{2}{\pi} \sqrt{I_s I_r} \cos\Psi \quad (10)$$

$$S_2' = K_2 \frac{2}{\pi} \sqrt{I_s I_r} \sin\Psi \quad (11)$$

When the expressions (10) and (11) are used, the amplitude of the S-polarized light component of the interference light and the amplitude of the P-polarized light component thereof are expressed by the following expression.

$$\sqrt{I_s I_r} \propto \sqrt{S_1'^2 + S_2'^2} \quad (12)$$

The expressions (8) and (9) are held based on the frequency simultaneous detection principle as shown in FIGS. 6A to 6E only when a difference $\delta f$ ($=|f_m - \Delta f_D|$) between the modulation frequency $f_m$ and the beat frequency $\Delta f_D$ of the interference light beam is equal to 0 ($\delta f=0$) or smaller than 1/B ($\delta f<1/B$). When $\delta f>1/B$, each of the values of $S_1$ and $S_2$ in the expressions (8) and (9) reduces to 0. Here, B indicates a frequency band of the CCDs 21 and 22. For example, when a frame rate of a CCD is 100 Hz, 1/B can be set to 100 (Hz). This condition ($\delta f=0$) or ($\delta f<1/B$) corresponds to "substantially equal" of "the interference frequency component corresponding to the beat frequency substantially equal to the modulation frequency of the intensity" in the present invention.

Therefore, when the modulation frequency $f_m$ of the intensity of the light beam and the amount of frequency shift $f_D'$ applied to the reference light R are known, it is possible to calculate the beat frequency $f_D$ ($\neq 0$) of the interference light included in the superimposed light L. In the measurement in this embodiment, the modulation frequency $f_m$ of the intensity of the light beam and the amount of frequency shift $f_D'$ applied to the reference light R are set and changed by the control portion 40, so they are known values.

As described above, the measurement is performed on various depth regions of the object to be measured O while the modulation frequency $f_m$ (j=1 to M) of the intensity of the light beam outputted from the broad-band light source 2 is changed. Therefore, a distribution of the moving velocity of the moving matter by which a beat frequency corresponding to each modulation frequency value is caused can be imaged.

[Operation and Effect]

According to the above-mentioned optical image measuring apparatus 1, it is possible to measure an x-y sectional image expressing a moving velocity distribution of the moving matter in the object to be measured O at each depth at a time without scanning in x-y directions. Therefore, the object to be measured O can be speedily measured over a wide range.

In the measurement on an image expressing a distribution such as a flow velocity distribution of blood flowing through a blood vessel of a living tissue, it is unnecessary to move the object to be measured in order to change the measurement region. Therefore, the object to be measured can be effectively measured over a wide range.

MODIFIED EXAMPLES IN FIRST EMBODIMENT

Hereinafter, modified examples in this embodiment will be described.

Modified Example 1

Figure 7:
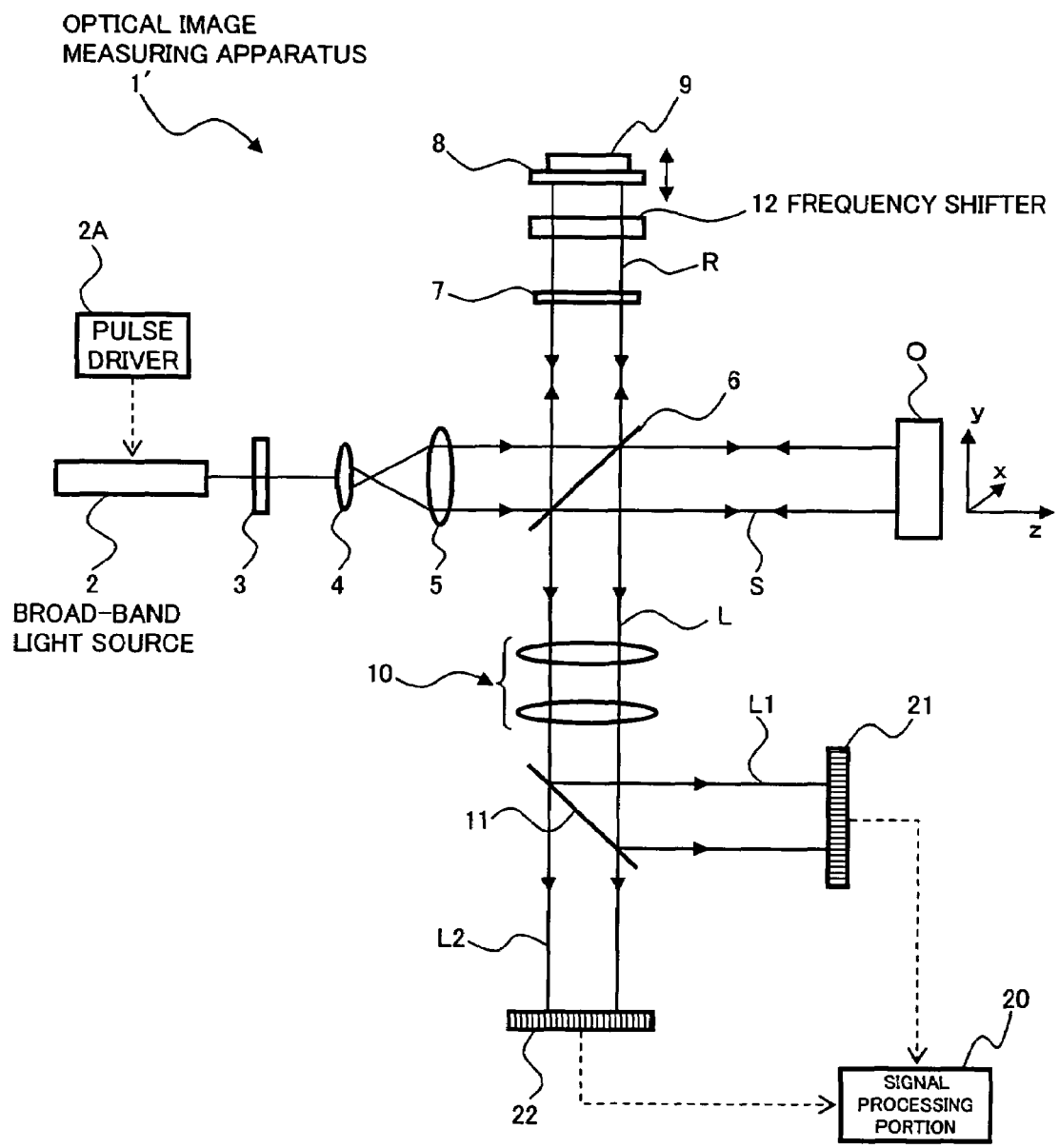
FIG. 7 is a schematic diagram showing Modified Example 1 of the optical image measuring apparatus according to the first embodiment of the present invention.

FIG. 7 illustrates a modified example of the optical image measuring apparatus 1. An optical image measuring apparatus 1' shown in FIG. 7 includes the same structure as that of the optical image measuring apparatus 1 except for a frequency shifter 12 disposed on the optical path of the reference light R. The frequency shifter 12 composes "frequency shifting means" in the present invention and shifts a frequency of the reference light R before and after it is reflected on the reference mirror 8. The frequency shifter 12 is composed of, for example, an optoelectronic modulator or an acoustooptic modulator.

The frequency shifter 12 is used to satisfy the above-mentioned condition ($f_D'>f_D$: the amount of frequency shift applied to the signal light S) related to the amount of frequency shift $f_D'$ applied to the reference light R, or in the case where it is difficult or impossible to detect the interference light, such as the case where the amount of frequency shift applied to the signal light S becomes too large by the Doppler effect caused by the moving matter and thus the beat frequency of the interference light is too high, the frequency shifter 12 is used to shift the frequency of the reference light R so as to bring the frequency thereof close to the frequency (of a part) of the signal light S. Note that the case where the amount of frequency shift applied to the signal light S becomes larger may be, for example, the case where the blood flow having a large velocity is in the −z direction (V=Vz) in FIG. 12.

For example, when the beat frequency of the interference light is too high, the control portion 40 controls the frequency shifter 12 to change the amount of frequency shift applied to the reference light R until a detection signal having a preferred frequency is outputted from each of the CCDs 21 and 22, thereby determining the preferable amount of frequency shift applied to the reference light R. When a clinical value related to a blood flow velocity or the like is known, it may be efficient to change a frequency in a range close to the amount of frequency shift corresponding to the clinical value. After the preferable amount of frequency shift applied to the reference light R is determined by the frequency shifter 12, an image of the object to be measured O is measured with this state.

According to this modified example, even when the moving matter is moving in the z-direction at large velocity, the effective measurement can be executed. Therefore, it is possible to use various objects to be measured as measurement targets.

The structure for shifting the frequency of the reference light R is not limited to the frequency shifter 12. The reference mirror 8 may be moved by the piezoelectric element 9 in the optical path direction of the reference light R to change the frequency of the reference light R. Although the frequency shifter 12 is disposed on the optical path of the reference light R, it may be disposed on the optical path of the signal light S. That is, the frequency shifting means in the present invention may be a structure for applying a relative frequency difference between the signal light S and the reference light R. A structure for canceling a part of the amount of frequency shift applied to a part of the signal light S propagating through the moving matter is more preferable.

Modified Example 2

Figure 8:
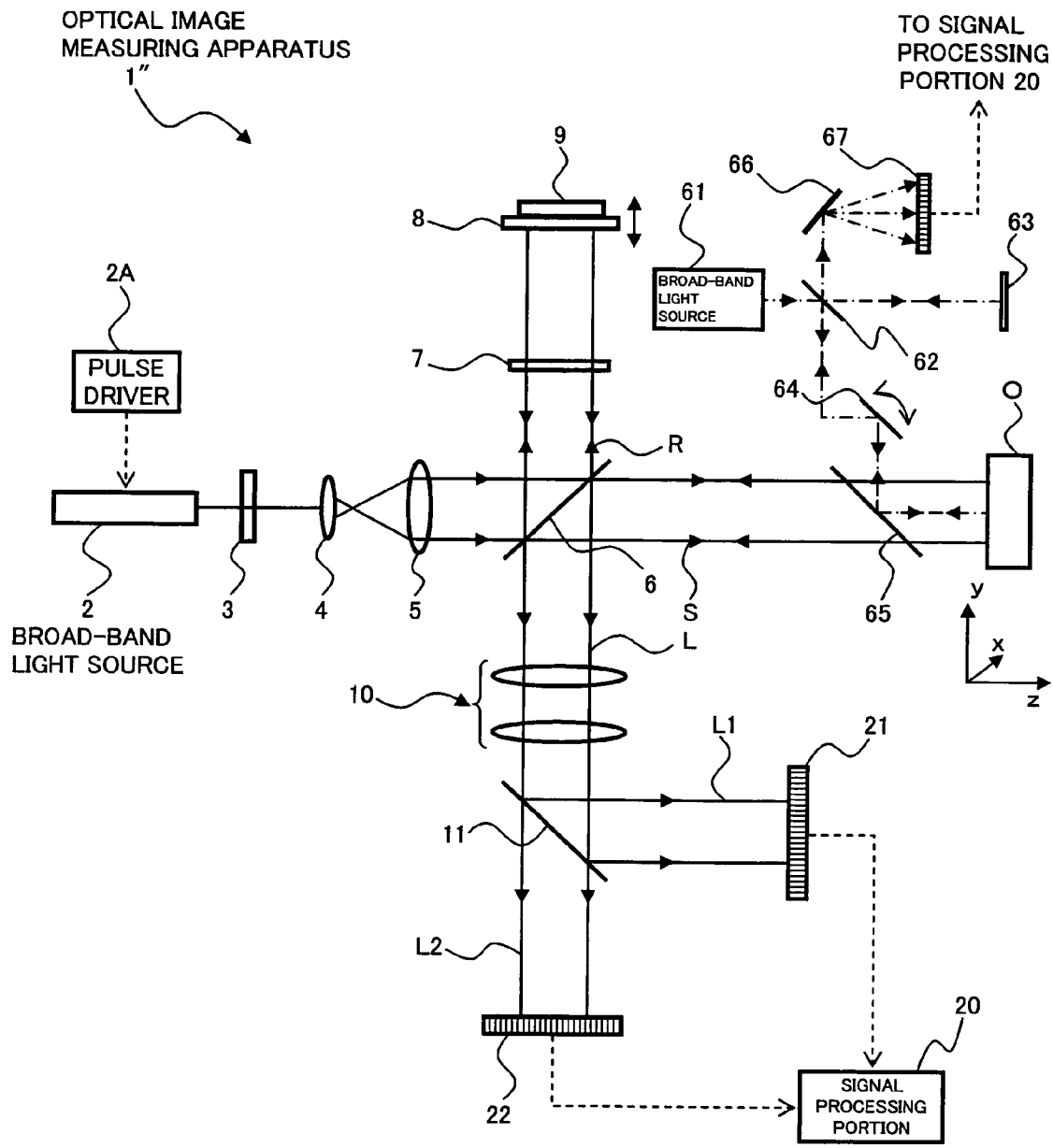
FIG. 8 is a schematic diagram showing Modified Example 2 of the optical image measuring apparatus according to the first embodiment of the present invention.

FIG. 8 illustrates a schematic structure of an optical image measuring apparatus 1" which is a second modified example in this embodiment. The optical image measuring apparatus 1" includes a structure capable of improving the precision of an arrangement interval of x-y tomographic images acquired by the measurement of the object to be measured O when a three-dimensional image is to be formed based on the x-y tomographic images, thereby acquiring the three-dimensional image or the like with high precision. Note that this modified example is disclosed in detail in Japanese Patent Application No. 2004-299036 made by the inventors of the present invention.

The optical image measuring apparatus 1" includes abroad-band light source 61, a half mirror 62, a fixed mirror 63, a galvanometer mirror 64, a wavelength filter 65, a diffraction grating 66, and a one-dimensional photo sensor array 67 in order to produce a measurement depth profile used to acquire measurement depths (z-coordinates) of a plurality of x-y tomographic images of the object to be measured O.

The broad-band light source 61 outputs a light beam having a wavelength different from that of the broad-band light source 2 for measurement (referred to as an "auxiliary light beam"). A part of the auxiliary light beam outputted from the broad-band light source 61 (referred to as "auxiliary signal light") is reflected on the half mirror 62 and propagates to the galvanometer mirror 64. A remaining part of the auxiliary light beam (referred to as "auxiliary reference light") passes through the half mirror 62 and propagates to the fixed mirror 63.

The galvanometer mirror 64 normally includes a reflecting mirror and a driver portion for driving the reflecting mirror to change the orientation of a reflective surface thereof. The galvanometer mirror 64 acts to perform scanning with the auxiliary signal light in the x-y directions. The wavelength filter 65 has a characteristic for transmitting the light beam from the broad-band light source 2 (the signal light S) and reflecting the auxiliary light beam from the broad-band light source 61 (the auxiliary signal light).

Therefore, the auxiliary signal light which is reflection light on the half mirror 62 is reflected on the galvanometer mirror 64 and then reflected on the wavelength filter 65. The object to be measured O is irradiated with the auxiliary signal light in addition to the signal light S. The auxiliary signal light and the signal light S with which the object to be measured O is irradiated are reflected on various depth (z-coordinate) regions and exit from the object to be measured O. Then, the auxiliary signal light is separated from the signal light S by the wavelength filter 65, reflected on the galvanometer mirror 64, and incident on the half mirror 62.

The auxiliary signal light which propagates through the object to be measured O and is incident on the half mirror 62 is superimposed on the auxiliary reference light reflected on the fixed mirror 63 to produce interference light (referred to as "auxiliary interference light").

The auxiliary interference light is separated into respective wavelength components by the diffraction grating 66.

The respective wavelength components are received by the one-dimensional photo sensor array 67. Each of photo sensors composing the one-dimensional photo sensor array 67 outputs a detection signal indicating a light intensity of each of the detected wavelength components (referred to as an "auxiliary detection signal") to the signal processing portion 20.

The signal processing portion 20 acquires a relationship between a wavelength and a light intensity of the auxiliary interference light, that is, an light intensity distribution (wavelength spectrum) of the auxiliary interference light based on the auxiliary detection signals corresponding to the respective wavelength components which are outputted from the one-dimensional photo sensor array 67.

Then, the signal processing portion 20 performs Fourier transform on the wavelength spectrum of the auxiliary interference light to acquire an intensity distribution of the auxiliary interference light based on the z-coordinate (measurement depth) of the object to be measured O as a variable. The intensity distribution corresponds to the measurement depth profile. The measurement depths related to the respective x-y tomographic images are calculated based on the intensity distribution. Such measurement depth calculation processing is executed at a rate of 1 MHz or more, that is, for a time of 1μ seconds or less.

During the measurement while scanning with the auxiliary signal light in the x-y directions is performed by the galvanometer mirror 64, a plurality of auxiliary detection signals corresponding to different scanning positions related to the x-y tomographic image acquired at each depth are inputted to the signal processing portion 20. The signal processing portion 20 calculates the measurement depth related to the corresponding x-y tomographic image based on the plurality of auxiliary detection signals.

The signal processing portion 20 arranges the plurality of acquired x-y tomographic images based on the measurement depths calculated in relation to the respective x-y tomographic images. Then, the signal processing portion 20 performs, for example, three-dimensional processing (interpolation processing) on the plurality of arranged x-y tomographic images to form a three-dimensional image of the object to be measured O and causes the display device to display the three-dimensional image.

In this modified example, when the plurality of x-y tomographic images are to be arranged in the measurement depth direction, the depths at which the respective x-y tomographic images are actually measured can be calculated. The plurality of x-y tomographic images are arranged based on the calculated depths, so the three-dimensional image or the like can be formed with high precision.

Modified Example 3

In this embodiment, the structure in which the pulse signal is periodically outputted from the pulse drive 2A to pulse-drive the broad-band light source 2 is employed to periodically modulate the intensity of the low-coherent light beam. However, the present invention is not limited to this structure. For example, when a (broad-band) light source capable of continuously emitting a low-coherent light beam is used and a shutter for periodically cutting off the continuously emitted light beam is provided between the light source and the polarizing plate 3, the intensity of the light beam can be periodically modulated. In this time, a high-speed shutter such as a liquid crystal shutter can be used as the shutter. It is desirable to control the frequency of open-and-close operation of the shutter by (the control portion 40 of) the signal processing portion 20.

Other Modified Examples

As described in this embodiment, the surface shape image and the internal shape image of the object to be measured O are acquired simultaneously with the processing for acquiring the image expressing the distribution of the moving velocity of the moving matter (shape images at (k=0) in (k=0 to 2m) are obtained). The shape images of the object to be measured O may be separately acquired. It is possible to form an image in which the shape image of the object to be measured O is synthesized with the image expressing the distribution of the moving velocity of the moving matter. For example, a shape image of a retina can be synthesized with the blood flow velocity distribution image. Therefore, an image fully reproducing the shape of the retina can be acquired.

In this embodiment, the light beam from the broad-band light source 2 is first converted to the linearly polarized light and then divided into the signal light S and the reference light R. Each of the signal light S and the reference light R may be converted to the linearly polarized light after the division of the light beam. In such a case, it is necessary to provide a polarizing plate on each of the optical path of the signal light S and the optical path of the reference light R, so such a structure becomes slightly more complex than the above-mentioned structure. Therefore, the structure in the embodiment may be more suitable in practical use.

In this embodiment, the polarization characteristic of the reference light R is converted to the circular polarization. It is also possible that the signal light S is converted to the circularly polarized light and superimposed on the reference light R which is the linearly polarized light. However, as described above, the reflection light of the signal light S which is reflected on the object to be measured O is weaker than the reference light R. Therefore, when the wavelength plate is disposed on the optical path of the signal light S, the signal light S passing therethrough weakens. The weakening of the intensity of the signal light S including information related to the object to be measured O may affect measurement sensitivity. Thus, the above-mentioned structure in which the polarization characteristic of the reference light R is converted to the circular polarization has an advantage. Note that the same is expected in the case where the frequency shifter is disposed.

It is unnecessary to periodically switch between the output and cutoff of the light beam from the broad-band light source 2 unlike the abode-mentioned structure. It is only necessary to periodically modulate the output intensity of the light beam. For example, it is possible to periodically switch between the 100% output intensity and the 50% output intensity of the light beam from the broad-band light source 2.

(Optical Image Measurement Using Contrast Agent)

The present invention is preferably used for optical image measurement using a contrast agent. Note that the optical image measurement using the contrast agent is disclosed in, for example, JP 2001-526650 A and JP 2002-504894 A.

Figure 13:
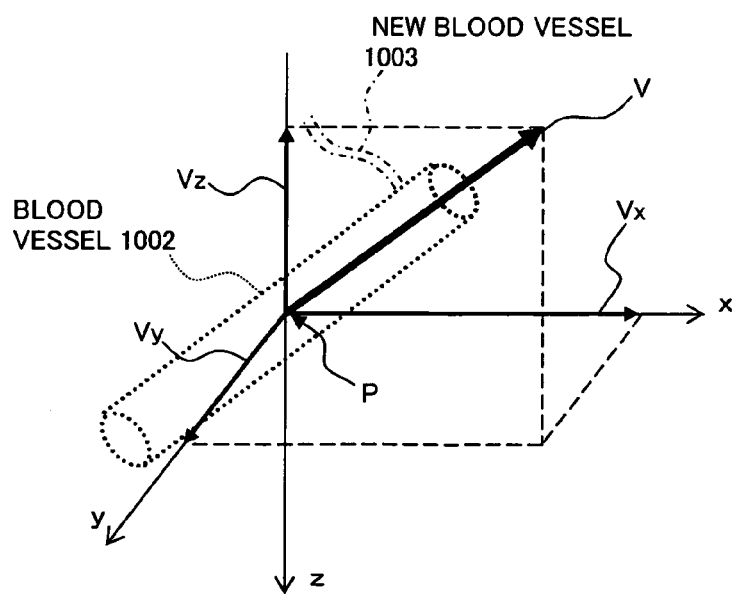
FIG. 13 is a schematic explanatory view showing a shape of a new blood vessel in the retina of the eye to be examined.
Figure 14:
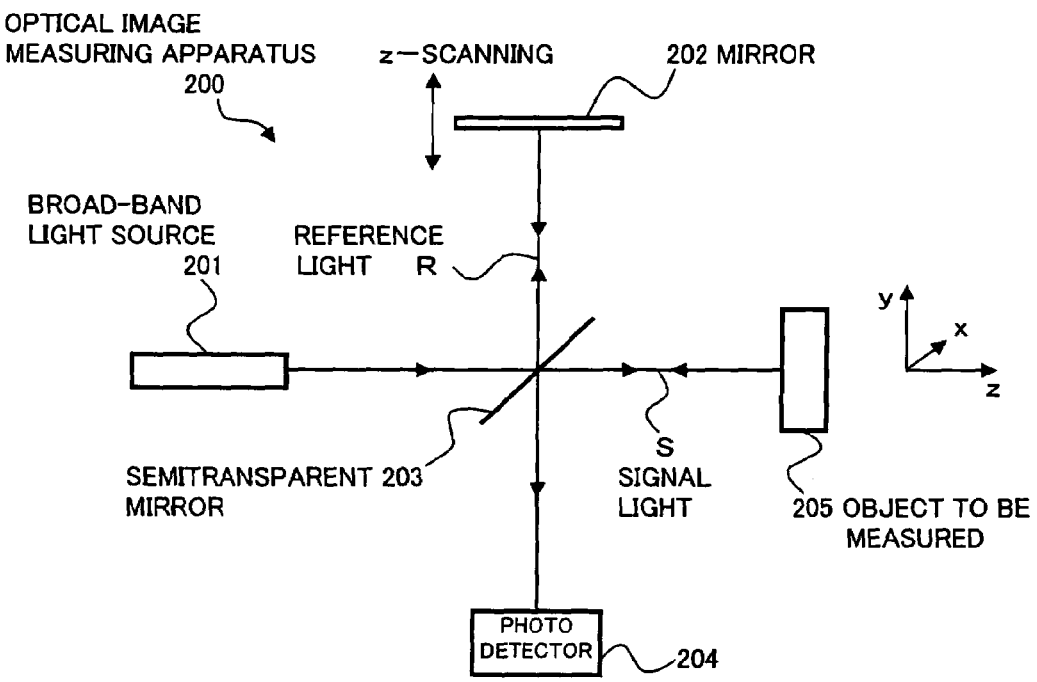
FIG. 14 is a schematic diagram showing a conventional optical image measuring apparatus.
Figure 15:
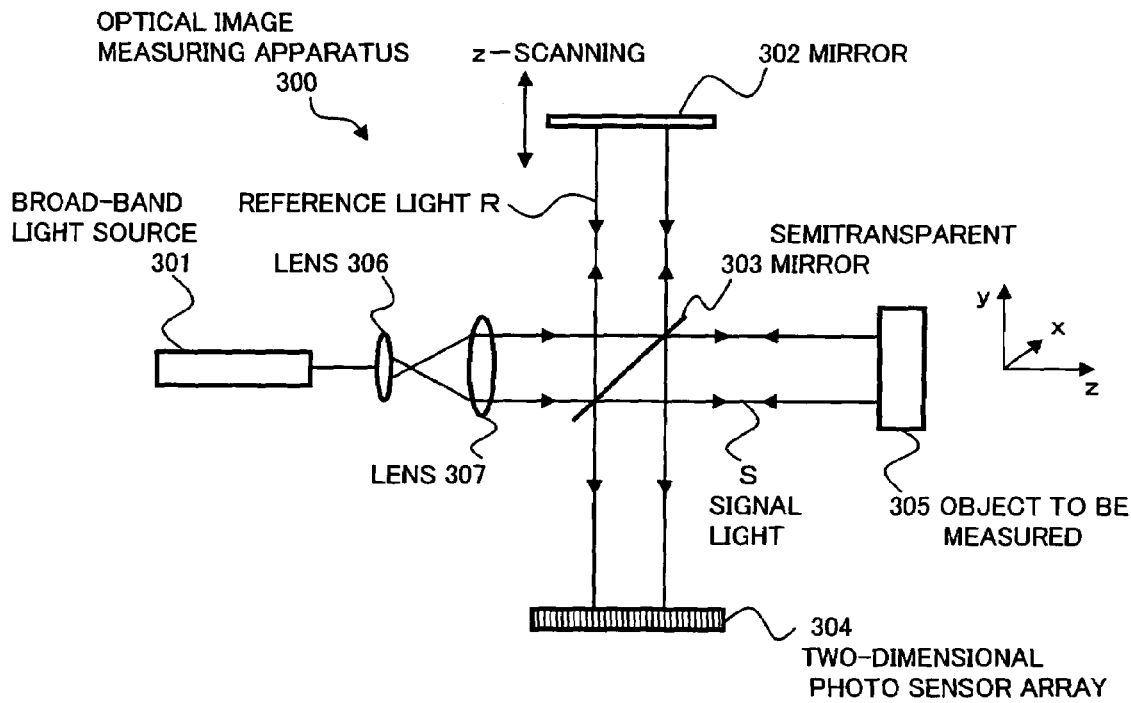
FIG. 15 is a schematic diagram showing a conventional optical image measuring apparatus.

The optical image measurement technique is effective for applications to an ophthalmologic field. This technique may be particularly effective for the photocoagulation therapy on a retina and a new blood vessel which is a lower tissue of the retina, the photodynamic therapy (PDT), and the like, which are performed for, for example, the age-related macular degeneration or the diabetic retinopathy. Here, the new blood vessel (see a new blood vessel 1003 shown in FIG. 13) is a new blood vessel grown from a healthy blood vessel region (blood vessel 1002) of the retina to a blood vessel region with a half-dead state. The new blood vessel is very weak, so when this is broken, heavy bleeding is caused, with the result that it is likely to lead to blindness. The many new blood vessels are grown with a complex state in which they are intertwined with one another, so it is desirable to grasp the three-dimensional arrangement state of the new blood vessels in order to suitably perform the photo-coagulation or the like. In some cases, normal retina tissues around the new blood vessels are burned by heat caused by a laser for the photocoagulation. Therefore, when the treatment is performed without grasping the detailed arrangement state of the new blood vessels, it is likely to cause a reduction in visual acuity. In particular, in the case of the treatment on the age-related macular degeneration, it is necessary to grasp the extremely detailed arrangement state of the new blood vessels in order to prevent the macular region from damaging. Hereinafter, an example of a mode for acquiring a three-dimensional image of the new blood vessel using the optical image measuring apparatus according to this embodiment will be described.

First, as in this embodiment, the method of imaging the blood flow velocity of a normal blood vessel and the blood flow velocity of the new blood vessel without any processing to display a blood flow velocity image can be employed as a first image acquisition mode. In such a case, in view of the fact that an end of the new blood vessel is closed and thus the blood flow velocity thereof is significantly slower than that of the normal blood vessel, it is desirable, for example, to display a region whose blood flow velocity is slow with a striking color (such as a red) in order to make the grasp of the arrangement state of the new blood vessels easy.

When the first image acquisition mode is used, a preferable image cannot be acquired in some cases depending on the arrangement state of the new blood vessels. For example, in view of the fact that the blood flow velocity of the new blood vessel which exists in the retina tissues is very slow, it is unlikely to distinguish between the new blood vessel and the retina tissues close thereto. In particular, the blood flow velocity in the vicinity of the tip end of the new blood vessel becomes (substantially) zero, so it may be completely indistinguishable from the surroundings.

Therefore, a second image acquisition mode for labeling (blood vessels including) the new blood vessel using a contrast agent is effective. The contrast agent used for such a purpose includes, for example, a contrast agent containing minute particles and a contrast agent having a function for absorbing light. In the second image acquisition mode, the contrast agent is injected to a person to be examined in advance. An image is acquired at a timing when the contrast agent reaches the blood vessel in the retina. Note that an image display manner is identical to that in the first image acquisition mode.

When the contrast agent containing minute particles is used, the signal S is scattered by the minute particles to reduce a light quantity thereof. Therefore, a part of the signal light S which propagates through the new blood vessel is detected as a light part having an intensity weaker than that of a part thereof which does not propagate through the new blood vessel. When the intensity difference is detected, the new blood vessel can be distinguished from surrounding retina tissues to perform imaging. On the other hand, even when the contrast agent having the function for absorbing light is used, the same imaging is possible.

When the contrast agent containing minute particles is used, it is possible to realize imaging based on a refractive index of the particles. For example, when a change in phase of the signal S which is caused based on the refractive index of the particles is detected, the new blood vessel can be distinguished from the surrounding retina tissues to perform imaging.

A method of forming an image based on a blood flow velocity difference between the new blood vessel and the normal blood vessel can be employed as a third image acquisition mode. When the new blood vessel is to be treated, it is necessary to perform sufficient photocoagulation on the base portion of the new blood vessel, that is, a portion at which the new blood vessel is connected to the normal blood vessel (connection point) in order to prevent the new blood vessel from growing again. The third image acquisition mode is a method of displaying a region whose blood flow velocity significantly changes with a striking color to specify a region to be treated.

A kind of used contrast agent and an image display manner are not limited to those described above and thus can be selected as appropriate. The object to be measured O which is subjected to the optical image measurement is not limited to the retina of a human eye and may be the retina of an arbitrary animal eye (that is, the above-mentioned eye to be measured).

Second Embodiment

Subsequently, a second embodiment of the present invention will be described. In this embodiment, the reference light included in the superimposed light is sampled using shutters.

[Structure of Apparatus]

Figure 9:
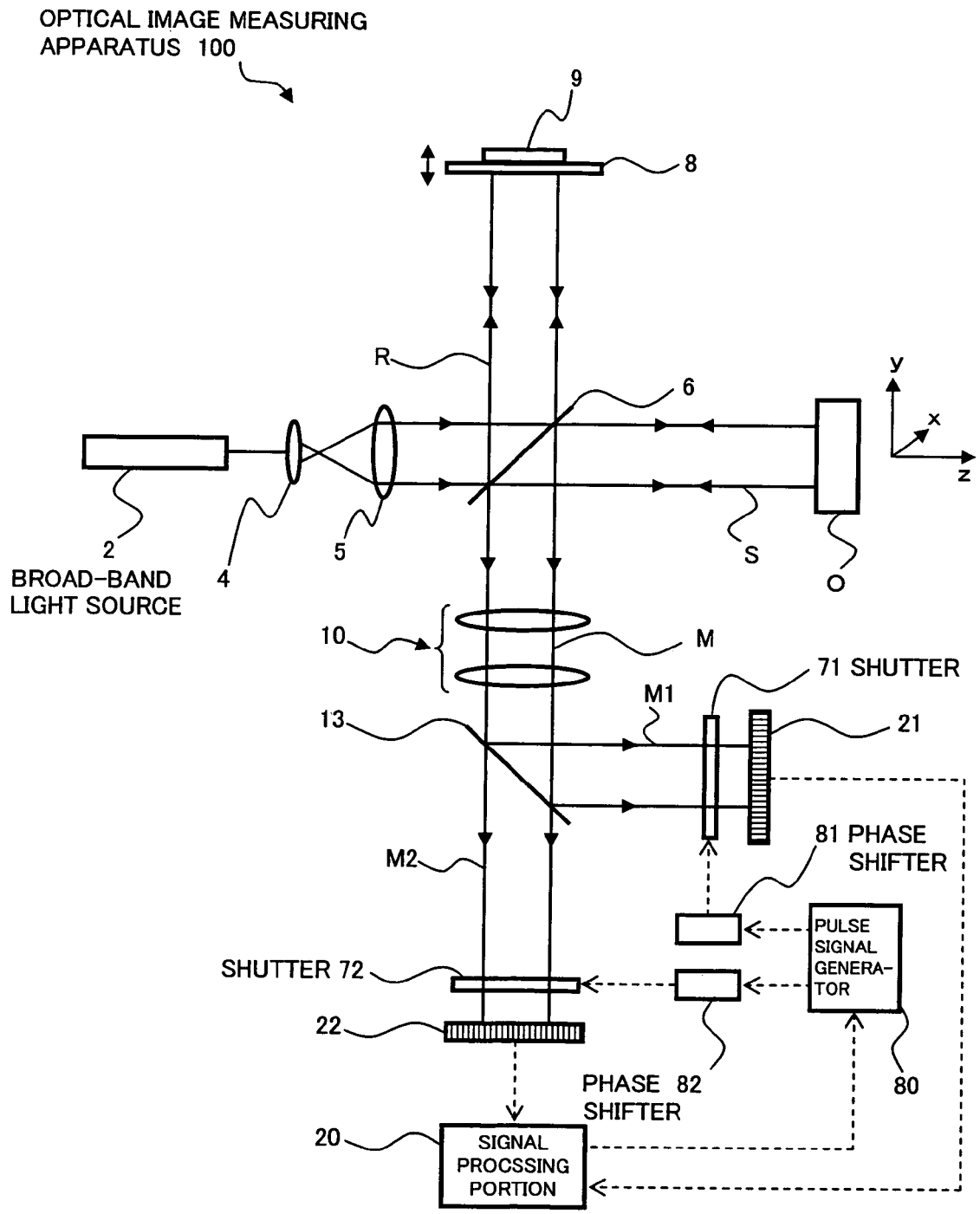
FIG. 9 is a schematic diagram showing an example of an optical image measuring apparatus according to a second embodiment of the present invention.
Figure 10:
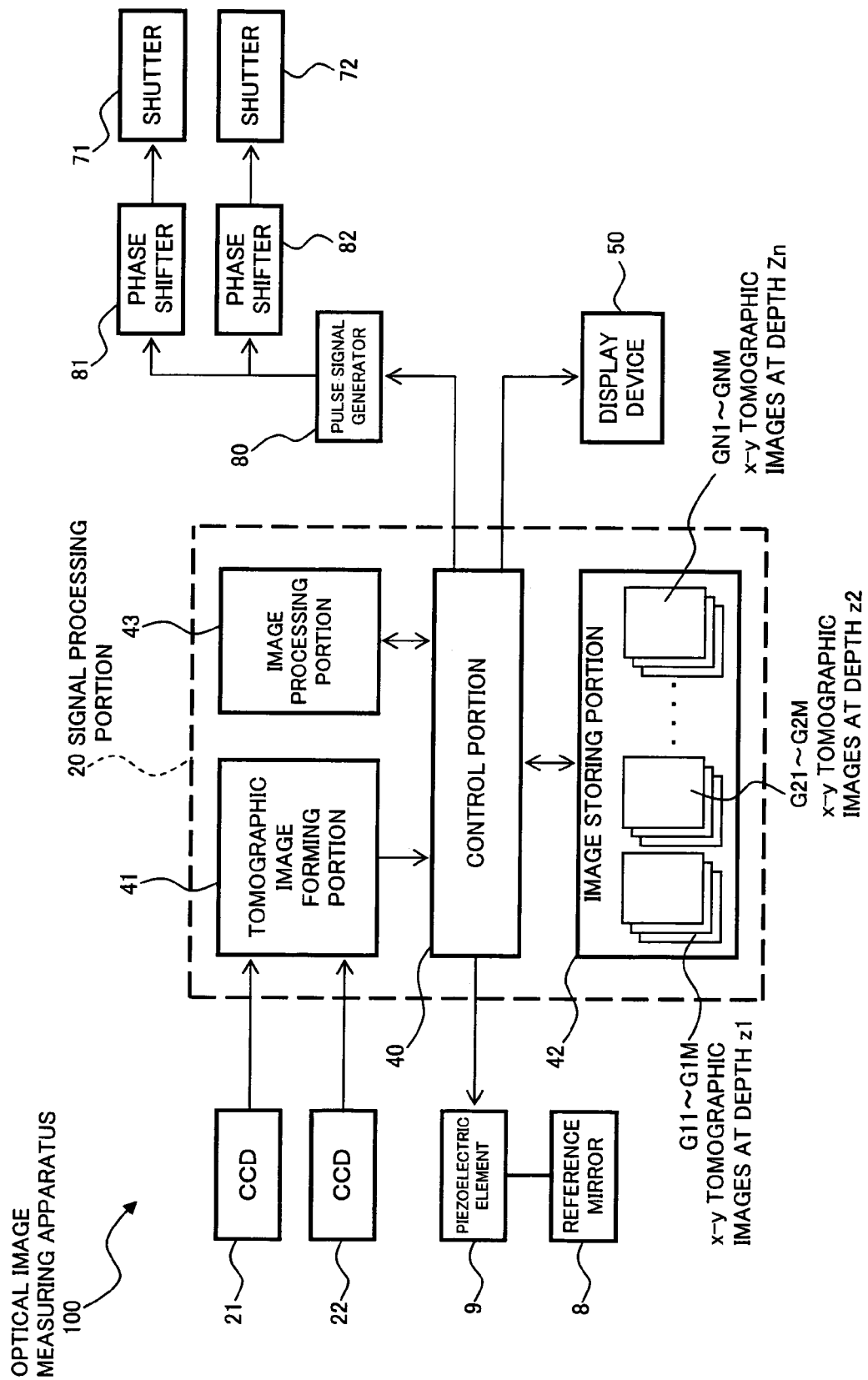
FIG. 10 is a block diagram showing an example of a control system of the optical image measuring apparatus according to the second embodiment of the present invention.

An optical image measuring apparatus according to this embodiment will be described. FIG. 9 illustrates an example of an optical system of the optical image measuring apparatus according to this embodiment and FIG. 10 illustrates an example of a control system thereof. Hereinafter, the same reference symbols are provided to the same constituent portions as those in the first embodiment.

[Structure of Optical System]

As shown in FIG. 9, an optical image measuring apparatus 100 includes the broad-band light source 2 (light source), the lenses 4 and 5 (increasing means), the half mirror 6 (light beam dividing means and superimposing means), the reference mirror 8 (reference object), and the piezoelectric element 9. The light source 2 is composed of a device for continuously generating low-coherent light, such as a SLD or a light emitting diode (LED). The lenses 4 and 5 convert a light beam from the light source 2 to a parallel light beam and increase a beam diameter thereof. The half mirror 6 divides the light beam into the signal light S and the reference light R and superimposes the signal light S and the reference light R on each other to produce superimposed light M. The reference mirror 8 is a total reflection mirror. The piezoelectric element 9 is used to move the reference mirror 8 in the optical path direction of the reference light R. The reference mirror 8 and the piezoelectric element 9 compose the "optical path length changing means" in the present invention.

As in Modified Example 1 of the first embodiment, a frequency shifter composed of an optoelectronic modulator, an acoustooptic modulator, or the like may be provided on, for example, the optical path of the reference light R.

The optical image measuring apparatus 100 further includes the imaging lens group 10, the beam splitter 13 (superimposed light dividing means), the CCDs 21 and 22 (two-dimensional photo-detection means), and shutters 71 and 72 (intensity modulating means). The imaging lens group 10 images the superimposed light M produced by the half mirror 6. The beam splitter 13 divides the superimposed light M into two superimposed light beams M1 and M2. Each of the CCDs 21 and 22 is the storage type two-dimensional photo sensor array. The shutters 71 and 72 are disposed immediately in front of the CCDs 21 and 22, respectively, and periodically cut off the superimposed light beams M1 and M2, respectively. Each of the shutters 71 and 72 is, for example, a high-speed shutter such as a liquid crystal shutter.

It is unnecessary that the shutters 71 and 72 are disposed immediately in front of the CCDs 21 and 22, respectively. The shutters 71 and 72 can be disposed at arbitrary positions on respective optical paths joining branch points of the superimposed light beams M1 and M2 separated by the beam splitter 13 with the CCDs 21 and 22. That is, it is only necessary that the shutters 71 and 72 be disposed in positions in which the respective superimposed light beams M1 and M2 can be cut off or transmitted to change the quantities of light beams which reach the CCDs 21 and 22.

The optical image measuring apparatus 100 further includes a pulse signal generator 80 and phase shifters 81 and 82. The pulse signal generator 80 generates pulse signals having a predetermined frequency in response to a control signal from the signal processing portion 20. The phase shifters 81 and 82 shift the phases of the pulse signals generated by the pulse signal generator 80 and output the pulse signals whose phases are shifted to each other to the shutters 71 and 72. The shutters 71 and 72 separately cut off or transmit the superimposed light beams M1 and M2, respectively, in response to the pulse signals from the phase shifters 81 and 82 as timing signals.

The shutters 71 and 72 periodically cut off the superimposed light beams M1 and M2 at a predetermined frequency, respectively, in response to the timing signals from the phase shifters 81 and 82 to sample the respective superimposed light beams M1 and M2. Therefore, the CCDs 21 and 22 periodically receive the superimposed light beams M1 and M2, respectively, perform photoelectric conversion thereon, and output detection signals which are results obtained by the conversion to the signal processing portion 20. As in the first embodiment, the signal processing portion 20 (image forming means) performs calculation processing described later to form an image of the object to be measured O.

The phase shifters 81 and 82 apply a predetermined phase difference between the open-and-close operations of the shutters 71 and 72. The phase difference may be, for example, 90° ($\pi/2$) as in the first embodiment or 180° ($\pi$) (this can be arbitrarily set). Therefore, the shutters 71 and 72 act to periodically modulate the intensities of the superimposed light beams M1 and M2 based on the predetermined phase difference. The phase difference applied by the phase shifters 81 and 82 may be changed by the signal processing portion 20 or the like. It is unnecessary to provide the phase shifter in front of each of the shutters 71 and 72. The phase shifter may be provided only in front of one of the shutters 71 and 72. For example, the phase shifter can be disposed only in front of the shutter 72, not in front of the shutter 71.

The beam diameter of the light beam emitted from the light source 2 is increased by the lenses 4 and 5. Then, the light beam is divided into the signal light S and the reference light R by the half mirror 6. The signal light S is incident on the object to be measured O and then incident on half mirror 6 again as a reflection light wave including information related to a surface shape and an internal shape of the object to be measured O. In particular, a part of the signal light S which propagates through a moving matter in the object to be measured O is subjected to frequency shift by the Doppler effect based on the moving velocity of the moving matter.

On the other hand, the reference light R is reflected on the reference mirror 8 vibrated in the optical path direction thereof by the piezoelectric element 9 and then incident on half mirror 6 again.

The part of the signal light S from the object to be measured O is reflected on the half mirror 6. Simultaneously, a part of the reference light R passes through the half mirror 6. At this time, a part of the signal lights which is subjected to the frequency shift caused by the moving matter is superimposed on the reference light R to produce interference light. The interference light has a beat frequency reflecting the amount of frequency shift applied to the signal light S. The superimposed light M including the interference light passes through the imaging lens group 10 and propagates to the beam splitter 13.

An optical path of the superimposed light M is divided into two by the beam splitter 13. The superimposed light beam M1 reflected on the beam splitter 13 is detected by the CCD 21 through the shutter 71. The superimposed light beam M2 passing through the beam splitter 13 is detected by the CCD 22 through the shutter 72.

It is desirable that a division ratio of the superimposed light M separated by the beam splitter 13, that is, an intensity ratio between the reflected superimposed light beam M1 and the transmitted superimposed light beam M2 be 1:1. Therefore, the intensity levels of the superimposed light beams M1 and M2 detected by the CCDs 21 and 22 are made equal to each other, so that the intensities of the interference light included in the superimposed light beams M1 and M2 become equal to each other. This is suitable to perform the calculation processing described later. Note that the division ratio of the superimposed light is not limited to this but can be set as appropriate.

[Structure of Control System]

Next, a structure of the control system of the optical image measuring apparatus 100 will be described with reference to FIG. 10.

As in the first embodiment (FIG. 2), the control system of the optical image measuring apparatus 100 includes the signal processing portion 20, the CCDs 21 and 22, the piezoelectric element 9 (and the reference mirror 8), and the display device 50. The operation of each part is substantially identical to that in the first embodiment.

As shown in FIG. 9, the optical image measuring apparatus 100 further includes the shutters 71 and 72, the pulse signal generator 80, and the phase shifters 81 and 82.

As in the first embodiment, the signal processing portion 20 includes the control portion 40 for controlling each part of the apparatus, the tomographic image forming portion 41 for forming x-y tomographic images of the object to be measured O based on the detection signals from the CCDs 21 and 22, the image storing portion 42 for storing the formed x-y tomographic images based on associations at respective depths, and the image processing portion 43 for forming an image such as a three-dimensional image of the object to be measured O based on the plurality of x-y tomographic images.

The control portion 40 controls the pulse signal generator 80 to generate pulse signals having one of various frequencies and output the pulse signals to the phase shifters 81 and 82. Therefore, the control portion 40 composes a "second modulation frequency changing means" in the present invention, for changing a frequency for cutting off the superimposed light beams M1 and M2 by the shutters 71 and 72. As in the first embodiment, the control portion 40 controls the piezoelectric element 9 to move the reference mirror 8 in the optical path direction of the reference light R.

[Measurement Processing]

Subsequently, measurement processing which is executed the object to be measured O by the optical image measuring apparatus 100 according to this embodiment will be described. The optical image measuring apparatus 100 executes substantially the same measurement processing as that in the first embodiment as shown in FIGS. 3 and 4.

In the optical image measuring apparatus 1 according to the first embodiment, the frequency at which the pulsed light beam is outputted is changed and the polarization characteristic of the light beam is controlled to sample the interference light beams included in the superimposed light beams L1 and L2. In addition, in the first embodiment, the frequency at which the pulsed light beam is outputted is changed to subsequently detect interference light beams having various beat frequencies which are included in the superimposed light beams L1 and L2 (interference light beams corresponding to moving matters having different moving velocities in the z-direction). Further, such measurement processing is executed while the position of the reference mirror 8 is changed, thereby measuring the x-y tomographic images of the object to be measured O at various measurement depth thereof. The three-dimensional image or the like is formed based on the plurality of x-y tomographic images.

In contrast to this, in the optical image measuring apparatus 100 according to this embodiment, the shutters 71 and 72 are provided in front of the CCDs 21 and 22 to cut off the superimposed light beams M1 and M2 at the same frequency. The predetermined phase difference is applied between the cutoff timings of the shutters 71 and 72 to sample interference light beams included in the superimposed light beams M1 and M2. Each of the detection signals outputted from the CCDs 21 and 22 includes interference frequency components corresponding to the plurality of interference light beams included in each of the superimposed light beams M1 and M2. Each of the interference frequency components has a frequency equal to the beat frequency of a corresponding interference light beam.

In the optical image measuring apparatus 100 according to this embodiment, the frequency for cutting off the superimposed light beams M1 and M2 by the shutters 71 and 72 is changed within a predetermined range including the beat frequencies of the interference light beams. Therefore, it is possible to form x-y tomographic images based on the plurality of interference frequency components included in the superimposed light beams M1 and M2.

As in the first embodiment, the measurement depth of the object to be measured O can be changed by a change in position of the reference mirror 8. The plurality of x-y tomographic images Gi1 to GiM are acquired at each measurement depth zi (i=1 to N). The plurality of x-y tomographic images Gi1 to GiM are synthesized with one another to form the two-dimensional image Gi (i=1 to N) related to each measurement depth zi. The two-dimensional images Gi are arranged corresponding to the respective measurement depths zi and subjected to image processing such as interpolation processing to form the three-dimensional image of the object to be measured O or the like. Therefore, the optical image measuring apparatus 100 according to this embodiment executes the same measurement processing as that in the first embodiment to image a moving velocity distribution of the moving matter in the object to be measured O.

[Operation and Effect]

In the optical image measuring apparatus 100 according to this embodiment, the x-y tomographic images are formed based on results obtained by detection of the interference light beams included in the superimposed light produced from the light beam whose beam diameter is increased by the lenses 4 and 5. Therefore, as in the first embodiment, it is possible to measure an x-y sectional image expressing a moving velocity distribution of the moving matter in the object to be measured O at each depth at a time without scanning in the x-y directions. Therefore, the object to be measured O can be speedily measured over a wide range.

In the measurement on an image expressing a distribution such as a flow velocity distribution of blood flowing through a blood vessel of a living tissue, it is unnecessary to move the object to be measured in order to change a measurement region. Therefore, the object to be measured can be effectively measured over a wide range.

[Modified Examples in Second Embodiment]

In the above-mentioned structure, the shutters for switching between light transmission and light cutoff are used for the intensity modulating means in the present invention. However, the present invention is not limited to the shutters. For example, it is possible to use a structure for changing light transmittance to sample the superimposed light beams M1 and M2, such as a structure for switching a display state of a liquid crystal panel of the liquid crystal shutter between a transmission state in which light transmittance is 100% and a semi-transmission state in which light transmittance is 50%.

For example, Modified Example 1 and Modified Example 2 of the first embodiment can be applied to the optical image measuring apparatus 100 according to this embodiment. In order to shift the frequency of the reference light R and the frequency of the signal light S relative to each other, it is possible to provide the frequency shifter on the optical path of the reference light R or to move the reference mirror 8. A shape image of the object to be measured O may be formed and synthesized with the velocity distribution image to produce a synthesized image.

The first and second embodiments described above in detail are merely examples for embodying the optical image measuring apparatus according to the present invention. Therefore, arbitrary modifications can be made without departing from the spirit of the present invention.

For example, when a distribution related to a moving matter having a predetermined moving velocity in a region of the object to be measured at a predetermined depth is to be acquired, it is possible that the reference mirror 8 is located in a position corresponding to the predetermined depth and then vibrated and the intensity of the light beam is modulated at a frequency corresponding to the predetermined moving velocity (or shutters are opened at closed at the frequency) to perform measurement.

The optical image measuring method according to the present invention is realized by, for example, the optical image measuring apparatus according to the above-mentioned embodiments. However, the optical image measuring method according to the present invention is not limited to the methods realized by the optical image measuring apparatus but realized by any structures made without departing from the spirit of the present invention. The optical image measuring method according to the present invention is not limited to examples realized by the optical image measuring apparatus and thus it is possible to use arbitrary modifications make without departing from the spirit of the present invention.

[Additional Items]

An example of another feature of the optical image measuring apparatus according to the invention and an example of another feature of the optical image measuring method according to the present invention will be described below.

[Additional Item 1]

In an aspect of an optical image measuring apparatus, the first modulation frequency changing means changes a frequency at which the intensity is modulated within a predetermined range including the beat frequency of the interference light.

[Additional Item 2]

In an aspect of an optical image measuring apparatus, the light beam outputting means includes:

Pulse driver means for outputting a drive pulse at a predetermined frequency; and a light source for outputting a low-coherent light beam at a predetermined frequency in response to the drive pulse.

Here, the "pulse driver means" includes the pulse driver 2A shown in, for example; FIG. 1 and the "light source" includes the broad-band light source shown in, for example, FIG. 1.

[Additional Item 3]

In an aspect of an optical image measuring apparatus, the light beam outputting means includes:

a light source for continuously outputting a low-coherent light beam; and a shutter for periodically cutting off the continuously outputted light beam.

Here, the "light source" includes the (broad-band) light source described in Modified Example 3 of the first embodiment and the "shutter" includes the shutter described in Modified Example 3 of the first embodiment.

[Additional Item 4]

In an aspect of an optical image measuring apparatus, the second modulation frequency changing means changes the modulation frequency within a predetermined range including the beat frequency of the interference light.

[Additional Item 5]

In an aspect of an optical image measuring apparatus, the intensity modulating means periodically modulates intensities of superimposed light beams propagating on a plurality of optical paths separated by the superimposed light dividing means based on a predetermined phase difference.

[Additional Item 6]

In an aspect of an optical image measuring apparatus, the intensity modulating means includes shutters for periodically cutting off the superimposed light beams.

[Additional Item 7]

In an aspect of an optical image measuring apparatus, the frequency shifting means includes a frequency shifter for shifting a frequency of the reference light, which is disposed on an optical path of the reference light.

[Additional Item 8]

In an aspect of an optical image measuring apparatus, the frequency shifting means vibrates or moves the reference object in an optical path direction of the reference light to apply frequency shift to the reference light.

In Additional Item 8, the "frequency shifting means" includes the reference mirror 8 and the piezoelectric element 9 as shown in, for example, FIG. 1.

[Additional Item 9]

In an aspect of an optical image measuring apparatus, the frequency shifting means shifts a frequency of the signal light and a frequency of the reference light relative to each other to cancel a part of the amount of frequency shift applied to a part of the signal light propagating through the moving matter.

[Additional Item 10]

In an aspect of an optical image measuring apparatus, the object to be measured is a living tissue, the moving matter is blood flowing through a blood vessel of the living tissue, and the moving velocity is a flow velocity of the blood.

In Additional Item 10, the "living tissue" corresponds to, for example, a retina.

[Additional Item 11]

An aspect of an optical image measuring method includes the step of shifting a frequency of the signal light and a frequency of the reference light relative to each other to cancel a part of the amount of frequency shift applied to a part of the signal light propagating through the moving matter.

What is claimed is:

1. An optical image measuring apparatus, comprising:
light beam outputting means for outputting a light beam whose intensity is periodically modulated at a modulation frequency, the light beam being low-coherent;
increasing means for increasing a beam diameter of the outputted light beam;
a first converting means for converting a polarization characteristic of the light beam to linear polarization;
light beam dividing means for dividing the light beam into signal light propagating to an object to be measured and reference light propagating to a reference object;
a second converting means for converting a polarization characteristic of one of the signal light and the reference light, which are linearly polarized light;
superimposing means for superimposing the signal light whose part propagating through a moving matter in the object to be measured is subjected to frequency shift and the reference light propagating through the reference object on each other to produce superimposed light including interference light having a beat frequency corresponding to a quantity of the frequency shift, in which one of the signal light and the reference light is the linearly polarized light acquired by the first converting means and the other thereof has the polarization characteristic acquired by the second converting means;
at least one two-dimensional photo-detection means for receiving a plurality of different polarized light components of the interference light included in the produced superimposed light, and outputting a detection signal including interference frequency components corresponding to beat frequencies of the interference light; and image forming means for forming a velocity distribution image expressing a moving velocity distribution of the moving matter based on an interference frequency component corresponding to a beat frequency substantially equal to the modulation frequency at which the intensity of the light beam is modulated by the light beam outputting means, among the interference frequency components included in the outputted detection signal.

2. An optical image measuring apparatus according to claim 1, further comprising optical path length changing means for changing an optical path length of the reference light to change a measurement depth of the object to be measured, wherein:
the two-dimensional photo-detection means outputs a plurality of detection signals corresponding to a plurality of measurement depths which are different from one another based on optical path lengths changed by the optical path length changing means;
the image forming means forms a plurality of two-dimensional velocity distribution images corresponding to the measurement depths based on the outputted detection signals corresponding to the plurality of measurement depths; and
the image forming means arranges the plurality of formed two-dimensional velocity distribution images in a measurement depth direction and performs image processing on the arranged two-dimensional velocity distribution images to form a three-dimensional velocity distribution image.

3. An optical image measuring apparatus according to claim 2, further comprising frequency shifting means for shifting a frequency of the signal light and a frequency of the reference light relative to each other.

4. An optical image measuring apparatus according to claim 3, further comprising display means for displaying the velocity distribution images formed by the image forming means.

5. An optical image measuring apparatus according to claim 4, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected in advance.

6. An optical image measuring apparatus according to claim 1, further comprising a first modulation frequency changing means for changing the modulation frequency at which the intensity of the light beam is modulated by the light beam outputting means, wherein:
the two-dimensional photo-detection means receives a plurality of superimposed light beams produced from the light beam whose intensity is modulated at different modulation frequencies changed by the first modulation frequency changing means and outputs a plurality of detection signals, each of which includes the interference frequency components;
the image forming means forms a plurality of two-dimensional images, each of which is based on an interference frequency component corresponding to a beat frequency substantially equal to a modulation frequency at which the intensity of the light beam is modulated by the light beam outputting means, in accordance with each of the plurality of outputted detection signals; and the image forming means synthesizes the plurality of formed two-dimensional images with one another to form a two-dimensional velocity distribution image.

7. An optical image measuring apparatus according to claim 6, further comprising optical path length changing means for changing an optical path length of the reference light to change a measurement depth of the object to be measured, wherein:
the two-dimensional photo-detection means outputs a plurality of detection signals corresponding to a plurality of measurement depths which are different from one another based on optical path lengths changed by the optical path length changing means;
the image forming means forms a plurality of two-dimensional velocity distribution images corresponding to the measurement depths based on the outputted detection signals corresponding to the plurality of measurement depths; and
the image forming means arranges the plurality of formed two-dimensional velocity distribution images in a measurement depth direction and performs image processing on the arranged two-dimensional velocity distribution images to form a three-dimensional velocity distribution image.

8. An optical image measuring apparatus according to claim 7, further comprising frequency shifting means for shifting a frequency of the signal light and a frequency of the reference light relative to each other.

9. An optical image measuring apparatus according to claim 8, further comprising display means for displaying the velocity distribution images formed by the image forming means.

10. An optical image measuring apparatus according to claim 9, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected in advance.

11. An optical image measuring apparatus according to claim 6, further comprising a polarization beam splitter for separating an S-polarized light component and a P-polarized light component of the interference light included in the superimposed light produced by the superimposing means from each other,
wherein the two-dimensional photo-detection means is provided on each of optical paths of the S-polarized light component and the P-polarized light component which are separated from each other.

12. An optical image measuring apparatus according to claim 11, further comprising optical path length changing means for changing an optical path length of the reference light to change a measurement depth of the object to be measured, wherein:
the two-dimensional photo-detection means outputs a plurality of detection signals corresponding to a plurality of measurement depths which are different from one another based on optical path lengths changed by the optical pat length changing means;
the image forming means forms a plurality of two-dimensional velocity distribution images corresponding to the measurement depths based on the outputted detection signals corresponding to the plurality of measurement depths; and the image forming means arranges the plurality of formed two-dimensional velocity distribution images in a measurement depth direction and performs image processing on the arranged two-dimensional velocity distribution images to form a three-dimensional velocity distribution image.

13. An optical image measuring apparatus according to claim 12, further comprising frequency shifting means for shifting a frequency of the signal light and a frequency of the reference light relative to each other.

14. An optical image measuring apparatus according to claim 13, further comprising display means for displaying the velocity distribution images formed by the image forming means.

15. An optical image measuring apparatus according to claim 14, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected in advance.

16. An optical image measuring apparatus according to claim 1, further comprising display means for displaying the velocity distribution images formed by the image forming means.

17. An optical image measuring apparatus according to claim 16, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected in advance.

18. An optical image measuring apparatus, comprising:
a light source for outputting a light beam which is low-coherent;
increasing means for increasing a beam diameter of the outputted light beam;
light beam dividing means for dividing the light beam whose beam diameter is increased into signal light propagating to an object to be measured and reference light propagating to a reference object;
superimposing means for superimposing the signal light whose part propagating through a moving matter in the object to be measured is subjected to frequency shift and the reference light propagating through the reference object on each other to produce superimposed light including interference light having a beat frequency corresponding to a quantity of the frequency shift;
intensity modulating means for periodically modulating an intensity of the produced superimposed light;
two-dimensional photo-detection means for receiving the superimposed light whose intensity is modulated, and outputting a detection signal including interference frequency components corresponding to beat frequencies of the interference light; and
image forming means for forming a velocity distribution image expressing a moving velocity distribution of the moving matter based on an interference frequency component corresponding to a beat frequency substantially equal to a modulation frequency at which the intensity of the superimposed light is modulated by the intensity modulating means, among the interference frequency components included in the outputted detection signal.

19. An optical image measuring apparatus according to claim 18, further comprising optical path length changing means for changing an optical path length of the reference light to change a measurement depth of the object to be measured, wherein:
the two-dimensional photo-detection means outputs a plurality of detection signals corresponding to a plurality of measurement depths which are different from one another based on optical path lengths changed by the optical path length changing means;
the image forming means forms a plurality of two-dimensional velocity distribution images corresponding to the measurement depths based on the outputted detection signals corresponding to the plurality of measurement depths; and
the image forming means arranges the plurality of formed two-dimensional velocity distribution images in a measurement depth direction and performs image processing on the arranged two-dimensional velocity distribution images to form a three-dimensional velocity distribution image.

20. An optical image measuring apparatus according to claim 19, further comprising frequency shifting means for shifting a frequency of the signal light and a frequency of the reference light relative to each other.

21. An optical image measuring apparatus according to claim 20, further comprising display means for displaying the velocity distribution images formed by the image forming means.

22. An optical image measuring apparatus according to claim 21, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected in advance.

23. An optical image measuring apparatus according to claim 18, further comprising a modulation frequency changing means for changing the modulation frequency at which the intensity of the superimposed light is modulated by the intensity modulating means, wherein:
the two-dimensional photo-detection means receives a plurality of superimposed light beams whose intensity is modulated at different modulation frequencies changed by the modulation frequency changing means and outputs a plurality of detection signals, each of which includes the interference frequency components;
the image forming means forms a plurality of two-dimensional images, each of which is based on an interference frequency component corresponding to a beat frequency substantially equal to a modulation frequency at which an intensity of a superimposed light beam is modulated by the intensity modulating means in accordance with each of the plurality of outputted detection signals; and
the image forming means synthesizes the plurality of formed two-dimensional images with one another to form a two-dimensional velocity distribution image.

24. An optical image measuring apparatus according to claim 23, further comprising optical path length changing means for changing an optical path length of the reference light to change a measurement depth of the object to be measured, wherein:
- the two-dimensional photo-detection means outputs a plurality of detection signals corresponding to a plurality of measurement depths which are different from one another based on optical path lengths changed by the optical path length changing means;
- the image forming means forms a plurality of two-dimensional velocity distribution images corresponding to the measurement depths based on the outputted detection signals corresponding to the plurality of measurement depths; and
- the image forming means arranges the plurality of formed two-dimensional velocity distribution images in a measurement depth direction and performs image processing on the arranged two-dimensional velocity distribution images to form a three-dimensional velocity distribution image.

25. An optical image measuring apparatus according to claim 24, further comprising frequency shifting means for shifting a frequency of the signal light and a frequency of the reference light relative to each other.

26. An optical image measuring apparatus according to claim 25, further comprising display means for displaying the velocity distribution images formed by the image forming means.

27. An optical image measuring apparatus according to claim 26, wherein:
- the object to be measured comprises at least one of a retina of an eye to be examined and a lower tissue of the retina; and
- the moving matter comprises one of blood flowing through a blood vessel of at least one of the retina and the lower tissue of the retina and blood containing a contrast agent injected in advance.

28. An optical image measuring apparatus according to claim 23, further comprising superimposed light dividing means for dividing an optical path of the superimposed light produced by the superimposing means into a plurality of optical paths,
wherein the two-dimensional photo-detection means receives each of a plurality of superimposed light beams propagating on the plurality of optical paths and outputs a detection signal.

29. An optical image measuring apparatus according to claim 28, further comprising optical path length changing means for changing an optical path length of the reference light to change a measurement depth of the object to be measured, wherein:
- the two-dimensional photo-detection means outputs a plurality of detection signals corresponding to a plurality of measurement depths which are different from one another based on optical path lengths changed by the optical path length changing means;
- the image forming means forms a plurality of two-dimensional velocity distribution images corresponding to the measurement depths based on the outputted detection signals corresponding to the plurality of measurement depths; and
- the image forming means arranges the plurality of formed two-dimensional velocity distribution images in a measurement depth direction and performs image processing on the arranged two-dimensional velocity distribution images to form a three-dimensional velocity distribution image.

30. An optical image measuring apparatus according to claim 29, further comprising frequency shifting means for shifting a frequency of the signal light and a frequency of the reference light relative to each other.

31. An optical image measuring apparatus according to claim 30, further comprising display means for displaying the velocity distribution images formed by the image forming means.

32. An optical image measuring apparatus according to claim 31, wherein:
- the object to be measured comprises at least one of a retina of an eye to be examined and a lower tissue of the retina; and
- the moving matter comprises one of blood flowing through a blood vessel of at least one of the retina and the lower tissue of the retina and blood containing a contrast agent injected in advance.

33. An optical image measuring apparatus according to claim 18, further comprising display means for displaying the velocity distribution images formed by the image forming means.

34. An optical image measuring apparatus according to claim 33, wherein:
- the object to be measured comprises at least one of a retina of an eye to be examined and a lower tissue of the retina; and
- the moving matter comprises one of blood flowing through a blood vessel of at least one of the retina and the lower tissue of the retina and blood containing a contrast agent injected in advance.

35. An optical image measuring method, comprising:
- a light beam outputting step for outputting a light beam whose intensity is periodically modulated at a modulation frequency, the light beam being low-coherent;
- an increasing step for increasing a beam diameter of the outputted light beam;
- a first converting step for converting a polarization characteristic of the light beam to linear polarization;
- a light beam dividing step for dividing the light beam into signal light propagating to an object to be measured and reference light propagating to a reference object;
- a second converting step for converting a polarization characteristic of one of the signal light and the reference light, which are linearly polarized light;
- a superimposing step for superimposing the signal light whose part propagating through a moving matter in the object to be measured is subjected to frequency shift and the reference light propagating through the reference object on each other to produce superimposed light including interference light having a beat frequency corresponding to a quantity of the frequency shift, in which one of the signal light and the reference light is the linearly polarized light acquired in the first converting step and the other thereof has the polarization characteristic acquired in the second converting step;
- a detection step for receiving a plurality of different polarized light components of the interference light included in the produced superimposed light by at least one two-dimensional photo-detection means, and outputting a detection signal including interference frequency components corresponding to beat frequencies of the interference light; and
- an image forming step for forming a velocity distribution image expressing a moving velocity distribution of the moving matter based on an interference frequency component corresponding to a beat frequency substantially equal to the modulation frequency at which the intensity of the light beam is modulated in the light beam outputting step, among the interference frequency components included in the outputted detection signal.

36. An optical image measuring method according to claim 35, further comprising an optical path length changing step for changing an optical path length of the reference light to change a measurement depth of the object to be measured, wherein:
the detection step includes outputting a plurality of detection signals corresponding to a plurality of measurement depths which are different from one another based on optical path lengths of the reference light; and
the image forming step includes:
forming a plurality of two-dimensional velocity distribution images corresponding to the measurement depths based on the outputted detection signals corresponding to the plurality of measurement depths; and
arranging the plurality of formed two-dimensional velocity distribution images in a measurement depth direction and performing image processing on the arranged two-dimensional velocity distribution images to form a three-dimensional velocity distribution image.

37. An optical image measuring method according to claim 36, further comprising a display step for displaying the velocity distribution images formed in the image forming step.

38. An optical image measuring method according to claim 37, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected in advance.

39. An optical image measuring method according to claim 35, wherein:
the light beam outputting step includes outputting the light beam while changing the modulation frequency at which the intensity of the light beam is modulated;
the detection step includes receiving a plurality of superimposed light beams produced from the light beam whose intensity is modulated at different modulation frequencies changed in the light beam outputting step and outputting a plurality of detection signals, each of which includes the interference frequency components; and
the image forming step includes:
forming a plurality of two-dimensional images, each of which is based on an interference frequency component corresponding to a beat frequency substantially equal to a modulation frequency at which the intensity of the light beam is modulated in the light beam outputting step, in accordance with each of the plurality of outputted detection signals; and
synthesizing the plurality of formed two-dimensional images with one another to form a two-dimensional velocity distribution image.

40. An optical image measuring method according to claim 39, further comprising an optical path length changing step for changing an optical path length of the reference light to change a measurement depth of the object to be measured, wherein:
the detection step includes outputting a plurality of detection signals corresponding to a plurality of measurement depths which are different from one another based on optical path lengths of the reference light; and
the image forming step includes:
forming a plurality of two-dimensional velocity distribution images corresponding to the measurement depths based on the outputted detection signals corresponding to the plurality of measurement depths; and
arranging the plurality of formed two-dimensional velocity distribution images in a measurement depth direction and performing image processing on the arranged two-dimensional velocity distribution images to form a three-dimensional velocity distribution image.

41. An optical image measuring method according to claim 40, further comprising a display step for displaying the velocity distribution images formed in the image forming step.

42. An optical image measuring method according to claim 41, wherein:
the object to be measured comprises at least one of a retina of an eye to be examined and a lower tissue of the retina; and
the moving matter comprises one of blood flowing through a blood vessel of at least one of the retina and the lower tissue of the retina and blood containing a contrast agent injected, in advance.

43. An optical image measuring method, comprising:
a step of outputting a light beam which is low-coherent;
an increasing step for increasing a beam diameter of the outputted light beam;
a light beam dividing step for dividing the light beam whose beam diameter is increased into signal light propagating to an object to be measured and reference light propagating to a reference object;
a superimposing step for superimposing the signal light whose part propagating through a moving matter in the object to be measured is subjected to frequency shift and the reference light propagating through the reference object on each other to produce superimposed light including interference light having a beat frequency corresponding to a quantity of the frequency shift;
an intensity modulating step for periodically modulating an intensity of the produced superimposed light;
a detection step for receiving the superimposed light whose intensity is modulated by a two-dimensional photo-detection means, and outputting a detection signal including interference frequency components corresponding to beat frequencies of the interference light; and
an image forming step for forming a velocity distribution image expressing a moving velocity distribution of the moving matter based on an interference frequency component corresponding to a beat frequency substantially equal to a modulation frequency at which the intensity of the superimposed light is modulated in the intensity modulating step, among the interference frequency components included in the outputted detection signal.

44. An optical image measuring method according to claim 43, further comprising an optical path length changing step for changing an optical path length of the reference light to change a measurement depth of the object to be measured, wherein:

the detection step includes outputting a plurality of detection signals corresponding to a plurality of measurement depths which are different from one another based on optical path lengths of the reference light; and the image forming step includes:
- forming a plurality of two-dimensional velocity distribution images corresponding to the measurement depths based on the outputted detection signals corresponding to the plurality of measurement depths; and
- arranging the plurality of formed two-dimensional velocity distribution images in a measurement depth direction and performing image processing on the arranged two-dimensional velocity distribution images to form a three-dimensional velocity distribution image.

45. An optical image measuring method according to claim 44, further comprising a display step for displaying the velocity distribution images formed in the image forming step.

46. An optical image measuring method according to claim 45, wherein:
- the object to be measured comprises at least one of a retina of an eye to be examined and a lower tissue of the retina; and
- the moving matter comprises one of blood flowing through a blood vessel of at least one of the retina and the lower tissue of the retina and blood containing a contrast agent injected in advance.

47. An optical image measuring method according to claim 43, wherein:
- the intensity modulating step includes modulating the intensity of the superimposed light while changing the modulation frequency;
- the detection step includes receiving a plurality of superimposed light beams whose intensity is modulated at different modulation frequencies changed by the second modulation frequency changing means and outputting a plurality of detection signals, each of which includes the interference frequency components; and
- the image forming step includes:
  - forming a plurality of two-dimensional images, each of which is based on an interference frequency component corresponding to a beat frequency substantially equal to a modulation frequency at which an intensity of a superimposed light beam is modulated in the intensity modulating step, in accordance with each of the plurality of outputted detection signals; and
  - synthesizing the plurality of formed two-dimensional images with one another to form a two-dimensional velocity distribution image.

48. An optical image measuring method according to claim 47, further comprising an optical path length changing step for changing an optical path length of the reference light to change a measurement depth of the object to be measured, wherein:
- the detection step includes outputting a plurality of detection signals corresponding to a plurality of measurement depths which are different from one another based on optical path lengths of the reference light; and
- the image forming step includes:
  - forming a plurality of two-dimensional velocity distribution images corresponding to the measurement depths based on the outputted detection signals corresponding to the plurality of measurement depths; and
  - arranging the plurality of formed two-dimensional velocity distribution images in a measurement depth direction and performing image processing on the arranged two-dimensional velocity distribution images to form a three-dimensional velocity distribution image.

49. An optical image measuring method according to claim 48, further comprising a display step for displaying the velocity distribution images formed in the image forming step.

50. An optical image measuring method according to claim 49, wherein:
- the object to be measured comprises at least one of a retina of an eye to be examined and a lower tissue of the retina; and
- the moving matter comprises one of blood flowing through a blood vessel of at least one of the retina and the lower tissue of the retina and blood containing a contrast agent injected in advance.

* * * * *